US008822181B2

(12) United States Patent
Torrent et al.

(10) Patent No.: US 8,822,181 B2
(45) Date of Patent: *Sep. 2, 2014

(54) PRODUCTION OF PROTEINS

(75) Inventors: Margarita Torrent, Barcelone (ES);
Miriam Bastida, Molins de Rei (ES);
Pablo Marzábal, Barcelone (ES);
Blanca Llompart, Barcelone (ES); $\text{M}^a$
Dolores Ludevid, Sant Just Desvern (ES)

(73) Assignee: ERA Biotech S.A., Barcelona (ES)

( * ) Notice: Subject to any disclaimer, the term of this patent is extended or adjusted under 35 U.S.C. 154(b) by 200 days.

This patent is subject to a terminal disclaimer.

(21) Appl. No.: 11/288,853

(22) Filed: Nov. 29, 2005

(65) Prior Publication Data

US 2006/0121573 A1    Jun. 8, 2006

(30) Foreign Application Priority Data

Nov. 29, 2004  (GB) .................................. 0426160.8

(51) Int. Cl.
*C12P 21/02* (2006.01)
*C12N 5/10* (2006.01)
*C12N 1/13* (2006.01)

(52) U.S. Cl.
USPC .......... 435/69.7; 435/348; 435/358; 435/365; 435/257.2; 435/369

(58) Field of Classification Search
None
See application file for complete search history.

(56) References Cited

U.S. PATENT DOCUMENTS

| | | | |
|---|---|---|---|
| 4,215,040 | A | 7/1980 | Hager |
| 6,642,437 | B1 | 11/2003 | Lemaux et al. |
| 7,575,898 | B2 | 8/2009 | Ludevid Múgica et al. |
| 8,163,880 | B2 | 4/2012 | Heifetz et al. |
| 2005/0221444 | A1 | 10/2005 | Williams et al. |
| 2005/0244924 | A1* | 11/2005 | Wagner et al. ............... 435/69.1 |
| 2006/0123509 | A1 | 6/2006 | Torrent et al. |
| 2007/0243198 | A1 | 10/2007 | Heifetz et al. |
| 2010/0083403 | A1 | 4/2010 | Ludevid Múgica et al. |
| 2011/0262478 | A1 | 10/2011 | Rybicki et al. |
| 2011/0305718 | A1 | 12/2011 | Ludevid Múgica et al. |
| 2012/0020992 | A1 | 1/2012 | Heifetz et al. |

FOREIGN PATENT DOCUMENTS

| | | |
|---|---|---|
| WO | WO 96/21029 | 7/1996 |
| WO | WO 02/086077 | 10/2002 |
| WO | WO 2004/003207 A1 | 1/2004 |
| WO | WO 2006/056484 A1 | 6/2006 |
| WO | WO 2007/096192 A2 | 8/2007 |
| WO | WO 2010/040847 A2 | 4/2010 |
| WO | WO 2011/147995 A1 | 12/2011 |

OTHER PUBLICATIONS

Torrent et al., Eukaryotic Protein Production in designed storage Organelles, *BMC Biology*, 7:5, pp. 1-14 (2009).
Engelhard et al., "The Insect Tracheal System: A Conduit for the Systemic Spread of *Autographa californica* M Nuclear Polyhedroisis Virus", *Proc. Natl. Acad. Sci., USA*, 91:3224-3227 (1994).
Geli et al., "Two Structural Domains Mediate Two Sequential Events in γ-Zein Targeting: Protein Endoplasmic Reticulum Retention and Protein Body Formation", *Plant Cell*, 6:1911-1922 (1994).
Herman and Larkins, "Protein Storage Bodies and Vacuoles", *Plant Cell*, 11:601-613 (1999).
Luckow et al., "Efficient Generation of Infectious Recombinant Baculoviruses by Site-Specific Transposon-Mediated Insertion of Foreign Genes into a Baculovirus Genome Propagated in *Escherichia coli*", *J. Virol*, 67:4566-4579 (1993).
Ludevid et al., "Subcellular Localtization of Glutelin-2 in Maize (*Zea mays* L.) Endosperm ", *Plant Mol. Biol.*, 3:277-234 (1984).
Matteucci et al., "Synthesis of Deoxyoligonucleotides on a Polymer Support", *J. A. Chem. Soc.*, 103:3185 (1981).
Odell et al., "Identification of DNA Sequences Required for Activity of the Cauliflower Mosaic Virus 35S Promoter", *Nature*, 313:810 (1985).
Paszkowski et al., "Direct Gene Transfer to Plants", *EMBO J.*, 3:2717-2722 (1989).
Shewry et al., "Cereal Seed Storage Proteins: Structures, Properties and Role in Grain Utilization", *J. Exp. Bot.*, 53 (370):947-958 (2002).
Torrent et al., "In Maize, Glutelin-2 and Low Molecular Weight Zeins are Synthesized by Membrane-Bound Polyribosomes and Translocated into Microsomal Membranes", *Plant Mol. Biol.*, 7:93-403 (1986).
Torrent et al., "Role of Structural Domains for Maize γ-zein Retention in *Xenopus* Oocytes ", *Planta*, 192 :512-518 (1994).
Esen, A., et al., "Tandem repeats in the N-terminal sequence of a proline-rich protein from corn endosperm," *Nature* 296(5858):678-679, Macmillan Journals Ltd., England (1982).
Losso, J.N., et al., "Perfusion Chromoatography Purification of a 15 kDa Rice Prolamin," *J. Agric. Food Chem.* 51:7122-7126, American Chemical Society, United States (2003).
Simon, R., et al., "Two Closely Related Wheat Storage Proteins Follow a Markedly Different Subcellular Route in *Xenopus laevis* Oocytes," *The Plant Cell* 2:941-950, American Society of Plant Physiologists, United States (1990).
Christianson D.D., et al., "Isolation and Chemical Composition of Protein Bodies and Matrix Proteins in Corn Endosperm," *Cereal Chemistry* 46(4):372-381, American Association of Cereal Chemists, United States (1969).
Domingos, A., et al., "Purification, cloning and autoproteolytic processing of an aspartic proteinase from *Centaurea calcitrapa*," *Eur. J. Biochem.* 267:6824-6831, FEBS, Netherlands (2000).
Torrent, M., et al., "Lysine-rich modified γ-zeins accumulate in protein bodies of transiently transformed maize endosperms," *Plant Molecular Biology* 34:139-149, Kluwer Academic Publishers, Netherlands (1997).

(Continued)

*Primary Examiner* — Nancy T Vogel

(74) *Attorney, Agent, or Firm* — Sterne, Kessler, Goldstein & Fox P.L.L.C.

(57) ABSTRACT

A method for forming a fusion protein that is expressed as a recombinant protein body-like assembly in host eukaryotic cells and organisms other than higher plants as host systems is disclosed. More particularly, peptides and proteins are fused to protein sequences that mediate the induction of recombinant protein body-like assembly (RPBLA) formation, are stably expressed and accumulated in these host cells after transformation with an appropriate vector. Methods for preparing the fusion protein are also disclosed.

44 Claims, 3 Drawing Sheets

(56) References Cited

OTHER PUBLICATIONS

Varner, J.E. and Schidlovsky, G., "Intracellular Distribution of Proteins in Pea Cotyledons" *Plant Physiology* 38: 139-144, American Society of Plant Physiologists, United States (1963).
Yang, D., et al., "Expression and localization of human lysozyme in the endosperm of transgenic rice," *Planta* 216:597-603, Springer-Verlag, Germany (2003).
Office Action mailed Aug. 19, 2008, in U.S. Appl. No. 11/289,264, Torrent et al., filed Nov. 29, 2005.
Office Action mailed Mar. 31, 2010, in U.S. Appl. No. 11/289,264, Torrent et al., filed Nov. 29, 2005.
Office Action mailed Nov. 23, 2010, in U.S. Appl. No. 11/289,264, Torrent et al., filed Nov. 29, 2005.
Office Action mailed May 20, 2011, in U.S. Appl. No. 11/289,264, Torrent et al., filed Nov. 29, 2005.
Office Action mailed Nov. 4, 2011, in U.S. Appl. No. 11/289,264, Torrent et al., filed Nov. 29, 2005.
Office Action mailed Oct. 1, 2009, in U.S. Appl. No. 11/709,527, Heifetz et al., filed Feb. 22, 2007.
Office Action mailed May 26, 2010, in U.S. Appl. No. 11/709,527, Heifetz et al., filed Feb. 22, 2007.
Office Action mailed May 11, 2009, in U.S. Appl. No. 11/709,527, Heifetz et al., filed Feb. 22, 2007.
Office Action mailed Oct. 23, 2012, in U.S. Appl. No. 11/166,579, Heifetz et al., filed Jun. 22, 2011.
International Search Reports dated Mar. 21, 2006.
International Search Reports dated Apr. 21, 2006.
International Search Reports dated Nov. 23, 2007.
International PCT Invitation with Annex Search Reports dated Jul. 31, 2007.
Altschuler et al., "The N- and C-Terminal Regions Regulate the Transport of Wheat γ-Gliadin through the Endoplasmic Reticulum in Xenopus Oocytes," *The Plant Cell*, 5:443-450 (Apr. 1993).
Cameron-Mills, "The Structure and Composition of Protein Bodies Purified from Barley Endosperm by Silica Sol Density Gradients", *Carlsberg Res. Commun*, 45:557-576 (1980).
Goytia, E. et al., "Production of Plum Pox Virus HC-Pro Functionally Active for Aphid Transmission in a Transient-Expression System", *Journ. of General Virol*., 37:3413-3423 (2006).
Kim et al., "Zein Protein Interactions, Rather Than the Asymmetric Distribution of Zein mRNAs on Endoplasmic Reticulum Membranes, Influence Protein Body Formation in Maize Endosperm," *The Plant Cell*, 14:655-672, 2002.
Mainieri et al., "Zeolin. A New Recombinant Storage Protein Constructed Using Maize γ-Zein and Bean Phaseolin," *Plant Physeolin*, 136:3447-3456 (2004).
Miflin, et al., "The Development of Protein Bodies in the Storage Tissues of Seeds: Subcellular Separations of Homogenates of Barley, Maize, and Wheat Endosperms and of Pea Cotyledons," *Journ. of Exp. Botany*, 32:199-219 (1981).
Philip et al., "Localization of β-glucuronidase in Protein Bodies of Transgenic Tobacco Seed by Fusion to an Amino Terminal Sequence of the Soybean Lectin Gene," *Plant Sci.*, 137:191-204 (1998).
Richard et al., "Transport and Deposition of Cereal Prolamin", *Plant Physiol. Biochem.*, 34:237-243 (1996).
Rosenberg et al., "Wheat (Wheat (*Triticum aestivum* L.) γ-Gliadin Accumulates in Dense Protein Bodies within the Endoplasmic Reticulum of Yeast," *Plant Physiol.*, 102:61-69 (1993).
Shukla et al., "Zein: The Industrial Protein from Corn", *Industrial Crops and Product*, 13:171-192 (2001).
Sojikul et al., "Á Plant Signal Peptide-Hepatitis B Surface Antigen Fusion Protein with Enhanced Stability and Immunogenicity Expressed in Plant Cells," *PNAS*, 100(5):2209-2214 (2003).
Takagi et al., "A Rice-Based Edible Vaccine Expressing Multiple T Cell Epitopes Induces Oral Tolerance for Inhibition of Th2-Mediated IgE Responses," *PNAS*, 102(48):17525-17530 (2005).
Wallace et al., "Aggregation of Lysine-Containing Zeins into Protein Bodies in *Xenopus* Oocytes," *Science*, 240:662-664 (1988).

* cited by examiner

A: *Saccharomyces cerevisiae*

B: *Pichia pastoris*

PRODUCTION OF PROTEINS

TECHNICAL FIELD

The present invention contemplates the production of recombinant peptides and proteins in eukaryotic cells and organisms other than higher plants as host systems. More particularly, peptides and proteins are fused to protein sequences that mediate the induction of recombinant protein body-like assembly (RPBLA) formation, are stably expressed and accumulated in these host systems after transformation with an appropriate vector.

BACKGROUND ART

The production of recombinant proteins for therapeutic, nutraceutical or industrial uses has enjoyed great success over the past decade. Different eukaryotic cells and organisms have been shown to be able to produce active protein-based therapeutics. Unfortunately, the high costs frequently derived from low recombinant protein production levels and/or from protein isolation and purification procedures, can invalidate their industrial application. Active research is done to improve both production levels and purification procedures by different approaches.

A new technology based on the fusion of a plant seed storage protein domain with the protein of interest (WO 2004/003207) has been developed to increase the stability and accumulation of recombinant proteins in higher plants. These storage proteins are specific to plant seeds wherein they stably accumulate in protein bodies (Galili et al., 1993, *Trends Cell Biol* 3:437-442).

The storage proteins are inserted into the lumen of the endoplasmic reticulum (ER) via a signal peptide and are assembled either in the endoplasmic reticulum developing specific organelles called ER-derived protein bodies (ER-PBs) or in protein storage vacuoles (PSV) (Okita and Rogers 1996 Annu. Rev. Plant Physiol Mol. Biol. 47: 327-50; Herman and Larkins 1999 Plant Cell 11:601-613; Sanderfoot and Raikel 1999 Plant Cell 11:629-642). Recombinant storage proteins have also been described to assemble in PB-like organelles in non-plant host systems as *Xenopus* oocytes and yeast.

Expression of cereal prolamins (the most abundant cereal storage proteins) has been described in *Xenopus* oocytes after injection of the corresponding mRNAs. This system has been used as a model to study the targeting properties of these storage proteins (Simon et al., 1990, *Plant Cell* 2:941-950; Altschuler et al., 1993, *Plant Cell* 5:443-450; Torrent et al., 1994, *Planta* 192:512-518) and to test the possibility of modifying the 19 kDa α-zein, a maize prolamin, by introducing the essential amino acids lysine and tryptophan into its sequence, without altering its stability (Wallace et al, 1988, *Science* 240:662-664).

Zeins, the complex group of maize prolamins, have also been produced in yeast with various objectives. Coraggio et al., 1988, *Eur J Cell Biol* 47:165-172, expressed native and modified α-zeins in yeast to study targeting determinants of this protein. Kim et al., 2002, *Plant Cell* 14: 655-672, studied the possible α-, β-, γ- and δ-zein interactions that lead to protein body formation. To address this question, they transformed yeast cells with cDNAs encoding these proteins. In addition, those authors constructed zein-GFP fusion proteins to determine the subcellular localization of zein proteins in the yeast cells. The yeast cells, then, were used as a model expression system to study zein properties. It is worth to noting that Kim et al., 2002, *Plant Cell* 14: 655-672, concluded that yeast is not a good model to study zein interactions because zeins, by themselves, were poorly accumulated in transformed yeast. The yeast cells were also used as a model to study the mechanisms that control the transport and protein body deposition of the wheat storage proteins called gliadins (Rosenberg et al., 1993, *Plant Physiol* 102:61-69).

Here we show that fusion of a protein sequence that mediates induction of recombinant protein body-like assemblies (RPBLAs), as for instance, prolamins or prolamin domains with a peptide or protein of interest (target) mediates the accumulation of those RPBLAs in cells of organisms such as fungi (which includes yeast), algae and animals. Interestingly, these fusion proteins are stably accumulated in animal cells, inside protein body-like organelles structures.

BRIEF SUMMARY OF THE INVENTION

The present invention provides a system and method for producing a fusion protein containing protein body-inducing sequence (PBIS) and a peptide or protein (often collectively referred to herein as polypeptide) of interest in eukaryotic cells other than higher plants such as animals fungi and algae as well as in cultured animal, fungal and algal cells in which the fusion proteins containing the peptide or protein of interest stably accumulate as recombinant protein body-like assemblies (RPBLAs). The PBIS are able to mediate the induction of RPBLA formation and protein entry and/or accumulation in these organelles, as for instance, natural and modified storage protein sequences with a peptide or protein of interest (targets).

The present invention provides, among others, a method for producing a product of interest in the form of a fusion protein, in eukaryotic cells other than higher plants as a host system that has been transformed with a nucleic acid sequence comprising a nucleic acid portion coding for the PBIS and a nucleic acid portion encoding a polypeptide product of interest.

In a particular embodiment, the nucleic acid sequence used for transformation comprises (i) a nucleic acid sequence coding for a PBIS, and (ii) a nucleic acid sequence comprising the nucleotide sequence coding for a product of interest. In one embodiment, the 3' end of nucleic acid sequence (i) is linked to the 5' end of said nucleic acid sequence (ii). In another embodiment, the 5' end of nucleic acid sequence (i) is linked to the 3' end of nucleic acid sequence (ii). Thus, the PBIS sequence can be at the N-terminus or the C-terminus of the fusion protein.

In another particular embodiment, the nucleic acid sequence used for transformation comprises, in addition to the before-mentioned nucleic acid sequences (i) and (ii), a nucleic acid sequence comprising the nucleotide sequence coding for a spacer amino acid sequence. The spacer amino acid sequence can be an amino acid sequence cleavable, or not cleavable, by enzymatic or chemical means. In a particular embodiment, the nucleic acid sequence (iii) is placed between the nucleic acid sequences (i) and (ii), e.g., the 3' end of nucleic acid sequence (iii) is linked to the 5' end of said nucleic acid sequence (ii). In another embodiment, the 5' end of said nucleic acid sequence (iii) is linked to the 3' end of nucleic acid sequence (ii).

Also, in a particular embodiment, the nucleic acid sequence used for transformation purposes encodes a specifically cleavable sequence and is as defined according to patent application WO 2004003207, that is co-assigned with the present application. Further, in another embodiment, the nucleic acid is in accord with patent application WO 2004003207, wherein the nucleic acid sequence coding for the amino acid sequence that is specifically cleavable by enzymatic or chemical means is absent. In a further embodiment, the fusion proteins can be a direct fusion between the PBIS and the peptide or protein of interest.

In a further embodiment, the method of the invention further comprises the isolation and purification of the fusion protein.

In yet another embodiment, the protein of interest is fused to a natural or modified storage protein, as for instance, natural or modified prolamins or prolamin domains. Examples of proteins of interest include any protein having therapeutic, nutraceutical, biocontrol, or industrial use. Illustrative proteins and peptides include, for example, a hormone such as calcitonin, growth hormone, and the like, antibodies such as monoclonal antibodies and fragments thereof, antigens such as those useful for vaccines against human immunodeficiency virus (HIV); hepatitis B surface or core proteins, gastroenteritis, coronavirus, and the like, protease inhibitors, antibiotics, collagen, human lactoferrin, cytokines, industrial enzymes, such as hydrolases, glycosidases, oxido-reductases, etc.

BRIEF DESCRIPTION OF THE DRAWINGS

In the drawings forming a portion of this disclosure,

FIG. 2E shows ER stained with the red fluorescent DsRed2-ER protein marker. FIG. 2F shows an overlaying of FIG. 2D and FIG. 2E showing co-localization of the RX3-Ct with DsRed2 in the ER and in the PBLS. Insets in FIGS. 2A and 2C show high magnification images of PBLS. Bars: 1 micron.

FIG. 3A shows the accumulation of RX3-EGF (lane c117) and RX3-hGH (lane c118) fusion proteins in transformed *Saccharomyces*. Equivalent amounts of total protein extracts from cells and media were analyzed by immunoblot using specific antibodies. Cells transformed with the pYX243 plasmid without insert were used as control (C). The bottom of each panel contains a schematic representation of the constructs coding for RX3-hGH and RX3-EGF fusion proteins.

FIG. 3B illustrates accumulation of hGH and RX3-hGH containing fusion proteins in *Pichia pastoris* by using two different signal peptides. Equivalent amounts of total protein extracts from transformed cells and media were analyzed by immunoblot using specific antibodies. C1 and C2 indicate cells transformed, respectively, with pPIC9 and pPIC3.5K plasmids used as controls. Schematic representations of the constructs c135 and c121 coding for RX3-hGH fusion protein and construct c136 coding for hGH are shown at the bottom of the panels. Molecular weight markers (in kDa) are indicated on the left of the figures. "y"=yeast cells; "m"=medium; "SPg"=signal peptide from gamma-zein; "RX3"=N-terminal proline-rich gamma-zein sequence without signal peptide; "EGF"=epidermal growth factor; "hGH"=human growth hormone; "Afprepro"=alfa factor prepro peptide.

Figure 1:
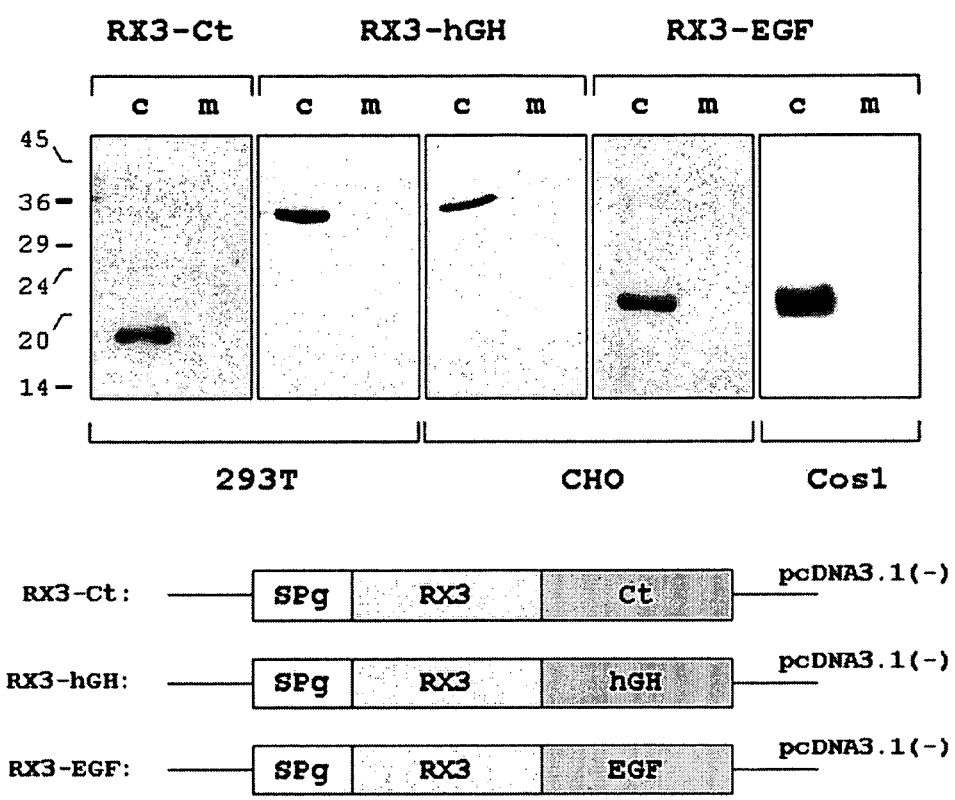
FIG. 1 is a photograph of a SDS/PAGE analysis showing the accumulation of fusion proteins including calcitonin (Ct), human growth hormone (hGH) and epidermal growth factor (EGF) as individual proteins of interest linked to the gamma-zein-derived RX3 protein body-inducing sequence in transfected mammalian cells. Fusion proteins RX3-Ct, RX3-hGH and RX3-EGF accumulated in transfected 293T, CHO and Cos1 cultured mammal cells are shown. Equivalent amounts of transfected mammal cells were extracted at 44 hours after transfection, and the corresponding total soluble proteins were analyzed by electrophoresis and western blot using the anti-gamma-zein antibody. Schematic representations of the constructs coding for RX3-Ct, RX3-hGH and RX3-EGF fusion proteins are also included. "c"=cells; "RX3"=N-terminal proline-rich gamma-zein sequence without signal peptide; "m"=medium. Molecular weight markers (in kDa) are indicated on the left.

The present invention has several benefits and advantages.

One benefit is that its use enables relatively simple and rapid expression of a desired recombinant protein in a non-higher plant eukaryotic cell of choice.

An advantage of the invention is that it provides a source of readily obtainable and purifiable recombinant protein because of the expression in RPBLAs.

Still further benefits and advantages will be apparent to the skilled worker from the discussion that follows.

DETAILED DESCRIPTION OF THE INVENTION

The contemplated recombinant proteins are fusion proteins that form recombinant protein body-like assemblies (RPBLAs) in the host cells in which they are expressed. The RPBLA formation is induced by storage protein domains that form high density deposits inside the cells. These dense deposits can accumulate in the cytosol, an endomenbrane system organelle, mitochondria, plastid or can be secreted. The recombinant protein body-like assemblies have a predetermined density that can differ among different fusion proteins, but is known for a particular fusion protein being prepared. That predetermined density of the RPBLAs is typically greater than that of substantially all of the endogenous host cell proteins present in the homogenate, and is typically about 1.1 to about 1.35 g/ml. The high density of novel RPBLAs is due to the general ability of the recombinant fusion proteins to assemble as multimers and accumulate. The contemplated RPBLAs are expressed in non-higher plant eukaryotes and are typically characterized by their densities as noted above. When expressed in animal cells, the RPBLAs are typically spherical in shape, have diameters of about 1 micron (µ) and have a surrounding membrane.

These fusion proteins comprise two polypeptide sequences linked together directly or indirectly by a peptide bond, in which one sequence is that of a protein body-inducing sequence (PBIS) linked to a polypeptide product (e.g., peptide or protein) of interest (target). PBIS are protein or peptide amino acid sequences that mediate the induction of RPBLA formation and the protein entry and/or accumulation in organelles. A PBIS and the host cell are preferably of different biological phyla. Thus, the PBIS is typically from a higher plant, a spermatophyte, whereas the host cell is a eukaryote that is other than a spermatophyte and can be an animal cell, as for instance mammalian or insect cells, a fungus/yeast, or an algal cell, all of which are of different phyla from spermatophytes. Illustrative, non-limiting examples of PBIS include storage proteins or modified storage proteins, as for instance, prolamins or modified prolamins, prolamin domains or modified prolamin domains. Prolamins are reviewed in Shewry et al., 2002 *J. Exp. Bot.* 53(370):947-958.

Preferred PBIS are those of prolamin compounds such as gamma-zein, alpha-zein or rice prolamin noted below.

gamma-zein, a maize storage protein whose DNA and amino acid residue sequences are shown hereinafter, is one of the four maize prolamins and represents 10-15 percent of the total protein in the maize endosperm. As other cereal prolamins, alpha- and gamma-zeins are biosynthesized in membrane-bound polysomes at the cytoplasmic side of the rough ER, assembled within the lumen and then sequestered into ER-derived protein bodies (Herman et al., 1999 *Plant Cell* 11:601-613; Ludevid et al., 1984 *Plant Mol. Biol.* 3:277-234; Torrent et al., 1986 *Plant Mol. Biol.* 7:93-403).

gamma-Zein is composed of four characteristic domains i) a peptide signal of 19 amino acids, ii) the repeat domain containing eight units of the hexapeptide PPPVHL (SEQ ID NO:1) (53 aa), iii) the ProX domain where proline residues alternate with other amino acids (29 aa) and iv) the hydrophobic cysteine rich C-terminal domain (111 aa).

The ability of gamma-zein to assemble in ER-derived RPBLAs is not restricted to seeds. In fact, when gamma-zein-gene was constitutively expressed in transgenic *Arabidopsis* plants, the storage protein accumulated within ER-derived PBLS in leaf mesophyl cells (Geli et al., 1994 *Plant Cell* 6:1911-1922). Looking for a signal responsible for the gamma-zein deposition into the ER-derived protein bodies (prolamins do not have KDEL signal), it has been demonstrated that the proline-rich N-terminal domain including the tandem repeat domain was necessary for ER retention and that the C-terminal domain was involved in protein bodies formation. However, the mechanisms by which these domains promote the protein body assembly are still unknown.

Inasmuch as protein bodies are appropriately so-named only in seeds, similar structures produced in other plant organs and in non-higher plants are referred to generally as recombinant protein body-like assemblies (RPBLAs).

Illustrative other useful prolamin-type sequences are shown in the Table below along with their GenBank identifiers.

| PROTEIN NAME | GENBANK ID |
|---|---|
| α-Zein (22 kD) | M86591 |
| Albumin (32 kD) | X70153 |
| β-Zein (14 kD) | M13507 |
| γ-Zein (27 kD) | X53514 |

| PROTEIN NAME | GENBANK ID |
|---|---|
| γ-Zein (50 kD) | AF371263 |
| δ-Zein (18 kD) | AF371265 |
| δ-Zein (10 kD) | U25674 |
| 7S Globulin or Vicilin type | NM_113163 |
| 11S Globulin or Legumin type | DQ256294 |
| Prolamin 13 kD | AB016504 |
| Prolamin 16 kD | AY427574 |
| Prolamin 10 kD | AF294580 |

Further useful sequences are obtained by carrying out a BLAST search in the all non-redundant GenBank CDS translations+PDB+SwissProt+PIR+PRF (excluding environmental samples) data base as described in Altschul et al., 1997 *Nucleic Acids Res.* 25:3389-3402 using a query such as those shown below:

```
                                                SEQ ID NO: 2
RX3 query
ppppvhlpppvhlpppvhlpppvhlpppvhlpppvhlpppvhvpppvhlp
ppp
```

```
                                                SEQ ID NO: 3
Alpha-zein
qqqqqflpalsqldvvnpvaylqqqllasnplalanvaayqqqqqlqqfl
palsqlamvnpaayl
```

```
                                                SEQ ID NO: 4
Rice prolamin query
qqvlspynefvrqqygiaaspflqsatfqlrnnqvwqqlalvaqqshcqd
inivqaiaqqlqlqqfgdly
```

An illustrative modified prolamin includes (a) a signal peptide sequence, (b) a sequence of one or more copies of the repeat domain hexapeptide PPPVHL (SEQ ID NO: 1) of the protein gamma-zein, the entire domain containing eight hexapeptide units; and (c) a sequence of all or part of the ProX domain of gamma-zein. Illustrative specific modified prolamins include the polypeptides identified below as R3, RX3 and P4 whose DNA and amino acid residue sequences are also shown below.

Particularly preferred prolamins include gamma-zein and its component portions as disclosed in published application WO2004003207, the rice rP13 protein and the 22 kDa maize alpha-zein and its N-terminal fragment. The DNA and amino acid residue sequences of the gamma-zein, rice and alpha-zein proteins are shown below.

Gamma-zein of 27 kD

```
                                                    SEQ ID NO: 5
DNA Sequence:
atgagggtgt tgctcgttgc cctcgctctc ctggctctcg    40
ctgcgagcgc cacctccacg catacaagcg gcggctgcgg    80
ctgccagcca ccgccgccgg ttcatctacc gccgccggtg   120
catctgccac ctccggttca cctgccacct ccggtgcatc   160
tccaccgcc ggtccacctg ccgccgccgg tccacctgcc    200
accgccggtc catgtgccgc cgccggttca tctgccgccg   240
ccaccatgcc actaccctac tcaaccgccc cggcctcagc   280
ctcatcccca gccacaccca tgcccgtgcc aacagccgca   320
tccaagcccg tgccagctgc agggaacctg cggcgttggc   360
agcacccga tcctgggcca gtgcgtcgag tttctgaggc    400
atcagtgcag cccgacggcg acgccctact gctcgcctca   440
gtgccagtcg ttgcggcagc agtgttgcca gcagctcagg   480
caggtggagc cgcagcaccg gtaccaggcg atcttcggct   520
tggtcctcca gtccatcctg cagcagcagc cgcaaagcgg   560
ccaggtcgcg gggctgttgg cggcgcagat agcgcagcaa   600
ctgacggcga tgtgcggcct gcagcagccg actccatgcc   640
cctacgctgc tgccggcggt gtccccacg cc              672
```

```
                                                            SEQ ID NO: 6
Protein Sequence:
Met Arg Val Leu Leu Val Ala Leu Ala Leu Leu Ala Leu Ala Ala Ser
 1               5                  10                  15
Ala Thr Ser Thr His Thr Ser Gly Gly Cys Gly Cys Gln Pro Pro Pro
            20                  25                  30
Pro Val His Leu Pro Pro Pro Val His Leu Pro Pro Pro Val His Leu
        35                  40                  45
Pro Pro Pro Val His Leu Pro Pro Pro Val His Leu Pro Pro Pro Val
    50                  55                  60
His Leu Pro Pro Pro Val His Val Pro Pro Pro Val His Leu Pro Pro
65                  70                  75                  80
Pro Pro Cys His Tyr Pro Thr Gln Pro Pro Arg Pro Gln Pro His Pro
                85                  90                  95
Gln Pro His Pro Cys Pro Cys Gln Gln Pro His Pro Ser Pro Cys Gln
            100                 105                 110
Leu Gln Gly Thr Cys Gly Val Gly Ser Thr Pro ILe Leu Gly Gln Cys
        115                 120                 125
Val Glu Phe Leu Arg His Gln Cys Ser Pro Thr Ala Thr Pro Tyr Cys
    130                 135                 140
Ser Pro Gln Cys Gln Ser Leu Arg Gln Gln Cys Cys Gln Gln Leu Arg
145                 150                 155                 160
Gln Val Glu Pro Gln His Arg Tyr Gln Ala Ile Phe Gly Leu Val Leu
                165                 170                 175
Gln Ser Ile Leu Gln Gln Gln Pro Gln Ser Gly Gln Val Ala Gly Leu
            180                 185                 190
Leu Ala Ala Gln Ile Ala Gln Gln Leu Thr Ala Met Cys Gly Leu Gln
        195                 200                 205
Gln Pro Thr Pro Cys Pro Tyr Ala Ala Ala Gly Gly Val Pro His Ala
    210                 215                 220

RX3
                                                            SEQ ID NO: 7
DNA Sequence:
atgagggtgt tgctcgttgc cctcgctctc ctggctctcg    40
ctgcgagcgc cacctccacg catacaagcg gcggctgcgg    80
ctgccagcca ccgccgccgg ttcatctacc gccgccggtg   120
catctgccac ctccggttca cctgccacct ccggtgcatc   160
tcccaccgcc ggtccacctg ccgccgccgg tccacctgcc   200
accgccggtc catgtgccgc cgccggttca tctgccgccg   240
ccaccatgcc actaccctac tcaaccgccc ggcctcagc    280
ctcatcccca gccacaccca tgcccgtgcc aacagccgca   320
tccaagcccg tgccagacc                          339

SEQ ID NO: 8
Protein Sequence:
Met Arg Val Leu Leu Val Ala Leu Ala Leu Leu Ala Leu Ala Ala Ser
 1               5                  10                  15
Ala Thr Ser Thr His Thr Ser Gly Gly Cys Gly Cys Gln Pro Pro Pro
            20                  25                  30
Pro Val His Leu Pro Pro Pro Val His Leu Pro Pro Pro Val His Leu
        35                  40                  45
Pro Pro Pro Val His Leu Pro Pro Pro Val His Leu Pro Pro Pro Val
    50                  55                  60
His Leu Pro Pro Pro Val His Val Pro Pro Pro Val His Leu Pro Pro
65                  70                  75                  80
Pro Pro Cys His Tyr Pro Thr Gln Pro Pro Arg Pro Gln Pro His Pro
                85                  90                  95
Gln Pro His Pro Cys Pro Cys Gln Gln Pro His Pro Ser Pro Cys Gln
            100                 105                 110
Tyr R3
                                                            SEQ ID NO: 9
DNA Sequence:
atgagggtgt tgctcgttgc cctcgctctc ctggctctcg    40
ctgcgagcgc cacctccacg catacaagcg gcggctgcgg    80
ctgccagcca ccgccgccgg ttcatctacc gccgccggtg   120
catctgccac ctccggttca cctgccacct ccggtgcatc   160
tcccaccgcc ggtccacctg ccgccgccgg tccacctgcc   200
accgccggtc catgtgccgc cgccggttca tctgccgccg   240

SEQ ID NO: 10
Protein Sequence:
Met Arg Val Leu Leu Val Ala Leu Ala Leu Leu Ala Leu Ala Ala Ser
 1               5                  10                  15
Ala Thr Ser Thr His Thr Ser Gly Gly Cys Gly Cys Gln Pro Pro Pro
            20                  25                  30
Pro Val His Leu Pro Pro Pro Val His Leu Pro Pro Pro Val His Leu
        35                  40                  45
```

-continued

```
Pro Pro Pro Val His Leu Pro Pro Pro Val His Leu Pro Pro Val
    50                  55                  60
His Leu Pro Pro Pro Val His Val Pro Pro Pro Val His Leu Pro Pro
65                  70                  75                  80
Pro Pro Cys His Tyr Pro Thr Gln Pro Pro Arg Tyr
            85                  90
```

P4

SEQ ID NO: 11

DNA Sequence:
```
atgagggtgt tgctcgttgc cctcgctctc ctggctctcg    40
ctgcgagcgc cacctccacg catacaagcg gcggctgcgg    80
ctgccagcca ccgccgccgg ttcatctgcc gccgccacca   120
tgccactacc ctacacaacc gccccggcct cagcctcatc   160
cccagccaca cccatgcccg tgccaacagc cgcatccaag   200
cccgtgccag acc                                213
```

SEQ ID NO: 12

Protein Sequence:
```
Met Arg Val Leu Leu Val Ala Leu Ala Leu Leu Ala Leu Ala Ala Ser
1               5                   10                  15
Ala Thr Ser Thr His Thr Ser Gly Gly Cys Gly Cys Gln Pro Pro Pro
                20                  25                  30
Pro Val His Leu Pro Pro Pro Cys His Tyr Pro Thr Gln Pro Pro
            35                  40                  45
Arg Pro Gln Pro His Pro Gln Pro His Pro Cys Pro Cys Gln Gln Pro
        50                  55                  60
His Pro Ser Pro Cys Gln Tyr
65                  70
```

X10

SEQ ID NO: 13

DNA Sequence:
```
atgagggtgt tgctcgttgc cctcgctctc ctggctctcg    40
ctgcgagcgc cacctccacg catacaagcg gcggctgcgg    80
ctgccaatgc cactaccta ctcaaccgcc ccggcctcag    120
cctcatcccc agccacaccc atgcccgtgc aacagccgc    160
atccaagccc gtgccagacc                         180
```

SEQ ID NO: 14

Protein Sequence:
```
Met Arg Val Leu Leu Val Ala Leu Ala Leu Leu Ala Leu Ala Ala Ser
1               5                   10                  15
Ala Thr Ser Thr His Thr Ser Gly Gly Cys Gly Cys Gln Cys His Tyr
                20                  25                  30
Pro Thr Gln Pro Pro Arg Pro Gln Pro His Pro Gln Pro His Pro Cys
            35                  40                  45
Pro Cys Gln Gln Pro His Pro Ser Pro Cys Gln Tyr
        50                  55                  60
``` rP13—rice prolamin of 13 kD homologous to the clone-AB016504 Sha et al., 1996 *Biosci. Biotechnol. Biochem.* 60(2):335-337; Wen et al., 1993 *Plant Physiol.* 101(3):1115-1116; Kawagoe et al., 2005 *Plant Cell* 17(4):1141-1153; Mullins et al., 2004 *J. Agric. Food Chem.* 52(8):2242-2246; Mitsukawa et al., 1999 *Biosci. Biotechnol. Biochem.* 63(11):1851-1858

SEQ ID NO: 15

Protein Sequence:
```
mkiifvfallaiaacsasaqfdvlgqsyrqyqlqspvllqqqvlspynef
vrqqygiaaspflqsatfqlrnnqvwqqlalvaqqshcqdinivqaiaqq
lqlqqfgdlyfdrnlaqaqallafnvpsrygiypryygapstittlggvl
```

SEQ ID NO: 16

DNA Sequence:
```
atgaagatcattttcgtctttgctctccttgctattgctgcatgcagcgc
ctctgcgcagtttgatgttttaggtcaaagttataggcaatatcagctgc
agtcgcctgtcctgctacagcaacaggtgcttagccatataatgagttc
gtaaggcagcagtatgggcataagcggcaagcccttcttgcaatcagctac
gtttcaactgagaaacaaccaagtctggcaacagctcgcgctggtggcgc
aacaatctcactgtcaggacattaacattgttcaggccatagcgcagcag
ctacaactccagcagtttggtgatctctactttgatcggaatctggctca
agctcaagctctgttggcttttaacgtgccatctagatatggtatctacc
ctaggtactatggtgcacccagtaccattaccaccttggcggtgtcttg
```

22aZt N-terminal fragment of the maize alpha-zein of 22 kD-V01475 Kim et al., 2002 *Plant Cell* 14(3):655-672; Woo et al., 2001 *Plant Cell* 13(10):2297-2317; Matsushima et al., 1997 *Biochim. Biophys. Acta* 1339(1):14-22; Thompson et al., 1992 *Plant Mol. Biol.* 18(4):827-833.

Protein Sequence (full length):

SEQ ID NO: 17
```
matkilallallalfvsatnafiipqcslapsaiipqflppvtsmgfehl
avqayrlqqalaasvlqqpinqlqqqslahltiqtiatqqqqqflpalsq
ldvvnpvaylqqqllasnplalanvaayqqqqqlqqflpalsql
```

DNA Sequence (full length)

SEQ ID NO: 18
```
atggctaccaagatattagccctccttgcgcttcttgccctttttgtgag
cgcaacaaatgcgttcattattccacaatgctcacttgctcctagtgcca
ttataccacagttcctcccaccagttacttcaatgggcttcgaacaccta
gctgtgcaagcctacaggctacaacaagcgcttgcggcaagcgtcttaca
acaaccaattaaccaattgcaacaacaatccttggcacatctaaccatac
aaaccatcgcaacgcaacagcaacaacagttcctaccagcactgagccaa
ctagatgtggtgaaccctgtcgcctacttgcaacagcagctgcttgcatc
caacccacttgctctggcaaacgtagctgcataccaacaacaacaacaat
tgcagcagtttctgccagcgctcagtcaacta
```

Examples of proteins of interest include any protein having therapeutic, nutraceutical, biocontrol, or industrial uses, such as, for example monoclonal antibodies (mAbs such as IgG, IgM, IgA, etc.) and fragments thereof, antigens for vaccines (human immunodeficiency virus, HIV; hepatitis B pre-surface, surface and core antigens, gastroenteritis corona virus, etc.), hormones (calcitonin, growth hormone, etc.), protease inhibitors, antibiotics, collagen, human lactoferrin, cytokines, industrial enzymes (hydrolases, glycosidases, oxidoreductases, and the like). Illustrative DNA and amino acid residue sequences for illustrative proteins of interest are provided below.

Salmon calcitonin BAC57417

SEQ ID NO: 19
Protein sequence:
kcsnlstcvlgklsqelhklqtyprtntgsgtpg

SEQ ID NO: 20
DNA sequence:
aagtgctccaacctctctacctgcgttcttggtaagctctctcaggagct
tcacaagctccagacttaccctagaaccaacactggttccggtacccctg
gt SEQ ID NO: 21
hEGF - Construction based in the AAF85790 without the signal peptide
Protein sequence:
nsdsecplshdgyclhdgvcmyiealdkyacncvvgyigercqyrdlkww
elr SEQ ID NO: 22
DNA sequence:
aactctgattcagaatgcccactcagtcacgacggatattgtcttcacga
tggggtatgcatgtacatcgaggccttggacaagtacgcatgtaattgtg
tagtgggatacattggtgaacgctgtcagtatcgagacttgaaatggtgg
gagcttaggtga hGH—Construction Based in the P01241 Without the Signal Peptide SEQ ID NO: 23
Protein sequence:
fptiplsrlfdnamlrahrlhqlafdtyqefeeayipkeqkysflqnpqt
slcfsesiptpsnreetqqksnlellrisllliqswlepvqflrsvfans
lvygasdsnvydllkdleegiqtlmgrledgsprtgqifkqtyskfdtns
hnddallknygllycfrkdmdkvetflrivqcrsvegscgf SEQ ID NO: 24
DNA sequence:
ttcccaaccattcccttatccaggcttttgacaacgctatgctccgcgc
ccatcgtctgcaccagctggcctttgacacctaccaggagtttgaagaag
cctatatcccaaaggaacagaagtattcattcctgcagaaccccccagacc
tccctctgtttctcagagtctattccgacaccctccaacagggaggaaac
acaacagaaatccaacctagagctgctccgcatctccctgctgctcatcc
agtcgtggctggagcccgtgcagttcctcaggagtgtcttcgccaacagc
ctggtgtacggcgcctctgacagcaacgtctatgacctcctaaaggacct
agaggaaggcatccaaacgctgatggggaggctggaagatggcagccccc
ggactgggcagatcttcaagcagacctacagcaagttcgacacaaactca
cacaacgatgacgcactactcaagaactacgggctgctctactgcttcag
gaaggacatggacaaggtcgagacattcctgcgcatcgtgcagtgccgct
ctgtggagggcagctgtggcttctga In another embodiment, the recombinant fusion protein further comprises in addition to the sequences of the PBIS and product of interest, a spacer amino acid sequence. The spacer amino acid sequence can be an amino acid sequence cleavable by enzymatic or chemical means or not cleavable. In a particular embodiment, the spacer amino acid sequence is placed between the PBIS and product of interest. An illustrative amino acid sequence is cleavable by a protease such as an enterokinase, Arg--C endoprotease, Glu--C endoprotease, Lys--C endoprotease, Factor Xa and the like. Alternatively, an amino acid sequence is encoded that is specifically cleavable by a chemical reagent, such as, for example, cyanogen bromide that cleaves at methionine residues.

In a further embodiment, the nucleic acid sequence used for transformation purposes is as disclosed according to co-assigned patent application WO 2004003207. Further, in another embodiment, the nucleic acid sequence is as disclosed according to patent application WO 2004003207, but the nucleic acid sequence coding for the cleavable amino acid sequence is absent.

In a preferred embodiment, the fusion proteins are prepared according to a method that comprises transforming a non-higher plant eukaryotic host cell system such as an animal, animal cell culture, fungi/yeast, insect or algae with a nucleic acid (DNA or RNA) sequence comprising (i) a first nucleic acid coding for a PBIS that is operatively linked in frame to (ii) a second nucleic acid sequence comprising the nucleotide sequence coding for a polypeptide product of interest; that is, the nucleic acid sequence that encodes the PBIS is chemically bonded (peptide bonded) to the sequence that encodes the polypeptide of interest such that both polypeptides are expressed from their proper reading frames. The host cell is maintained for a time period and under culture conditions suitable for expression of the fusion protein and assembly of the expressed fusion protein into recombinant protein body-like assemblies (RPBLAs). Upon expression, the resulting fusion protein accumulates in the transformed host-system as high density recombinant protein body-like assemblies. The fusion protein can then be recovered from the host cells or the host cells containing the fusion protein can be used as desired, as for an animal food containing an added nutrient or supplement. The fusion protein can be isolated as part of the RPBLAs or free from the RPBLAs.

Culture conditions suitable for expression of the fusion protein are typically different for each type of host cell. However, those conditions are known by skilled workers and are readily determined. Similarly, the duration of maintenance can differ with the host cells and with the amount of fusion protein desired to be prepared. Again, those conditions are well known and can readily be determined in specific situations. Additionally, specific culture conditions can be obtained from the citations herein.

In one embodiment, the 3' end of the first nucleic acid sequence (i) is linked (bonded) to the 5' end of the second nucleic acid sequence (ii). In other embodiment, the 5' end of the first nucleic acid sequence (i) is linked (bonded) to the 3' end of the second nucleic acid sequence (ii). In another embodiment, the PBIS comprises a storage protein or a modified storage protein, a fragment or a modified fragment thereof.

In another particular embodiment, a fusion protein is prepared according to a method that comprises transforming the host cell system such as an animal, animal cell culture, fungi/yeast or algae with a nucleic acid sequence comprising, in addition to the nucleic acid sequences (i) and (ii) previously mentioned, an in frame nucleic acid sequence (iii) that codes for a spacer amino acid sequence. The spacer amino acid sequence can be an amino acid sequence cleavable by enzymatic or chemical means or not cleavable, as noted before. In one particular embodiment, the nucleic acid sequence (iii) is placed between said nucleic acid sequences (i) and (ii), e.g., the 3' end of the third nucleic acid sequence (iii) is linked to the 5' end of the second nucleic acid sequence (ii). In another embodiment, the 5' end of the third nucleic acid sequence (iii) is linked to the 3' end of the second nucleic acid sequence (ii).

A nucleic acid sequence (segment) that encodes a previously described fusion protein molecule or a complement of that coding sequence is also contemplated herein. Such a nucleic acid segment is present in isolated and purified form in some preferred embodiments.

In living organisms, the amino acid residue sequence of a protein or polypeptide is directly related via the genetic code to the deoxyribonucleic acid (DNA) sequence of the gene that codes for the protein. Thus, through the well-known degeneracy of the genetic code additional DNAs and corresponding RNA sequences (nucleic acids) can be prepared as desired that encode the same fusion protein amino acid residue sequences, but are sufficiently different from a before-discussed gene sequence that the two sequences do not hybridize at high stringency, but do hybridize at moderate stringency.

High stringency conditions can be defined as comprising hybridization at a temperature of about 50°-55° C. in 6×SSC and a final wash at a temperature of 68° C. in 1-3×SSC. Moderate stringency conditions comprise hybridization at a temperature of about 50° C. to about 65° C. in 0.2 to 0.3 M NaCl, followed by washing at about 50° C. to about 55° C. in 0.2×SSC, 0.1% SDS (sodium dodecyl sulfate).

A nucleic sequence (DNA sequence or an RNA sequence) that (1) itself encodes, or its complement encodes, a fusion protein containing a protein body-inducing sequence (PBIS) and a polypeptide of interest is also contemplated herein. As is well-known, a nucleic acid sequence such as a contemplated nucleic acid sequence is expressed when operatively linked to an appropriate promoter in an appropriate expression system as discussed elsewhere herein.

Different hosts often have preferences for a particular codon to be used for encoding a particular amino acid residue. Such codon preferences are well known and a DNA sequence encoding a desired fusion protein sequence can be altered, using in vitro mutagenesis for example, so that host-preferred codons are utilized for a particular host in which the fusion protein is to be expressed.

A recombinant nucleic acid molecule such as a DNA molecule, comprising a vector containing one or more regulatory sequences (control elements) such as a promoter suitable for driving the expression of the gene in a compatible eukaryotic host cell organism operatively linked to an exogenous nucleic acid segment (e.g., a DNA segment or sequence) that defines a gene that encodes a contemplated fusion protein, as discussed above, is also contemplated in this invention. More particularly, also contemplated is a recombinant DNA molecule that comprises a vector comprising a promoter for driving the expression of the fusion protein in host organism cells operatively linked to a DNA segment that defines a gene encodes a protein body-inducing sequence (PBIS) linked to a polypeptide of interest. That recombinant DNA molecule, upon suitable transfection and expression in a host eukaryotic cell, provides a contemplated fusion protein as RPBLAs.

As is well known in the art, so long as the required nucleic acid, illustratively DNA sequence, is present, (including start and stop signals), additional base pairs can usually be present at either end of the DNA segment and that segment can still be utilized to express the protein. This, of course, presumes the absence in the segment of an operatively linked DNA sequence that represses expression, expresses a further product that consumes the fusion protein desired to be expressed, expresses a product that consumes a wanted reaction product produced by that desired fusion protein, or otherwise interferes with expression of the gene of the DNA segment.

Thus, so long as the DNA segment is free of such interfering DNA sequences, a DNA segment of the invention can be about 500 to about 15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known. Such long DNA segments are not preferred, but can be used.

A DNA segment that encodes a before-described fusion protein can be synthesized by chemical techniques, for example, the phosphotriester method of Matteucci et al. (1981) *J. Am. Chem. Soc.*, 103:3185. Of course, by chemically synthesizing the coding sequence, any desired modifications can be made simply by substituting the appropriate bases for those encoding the native amino acid residue sequence. However, DNA segments including sequences specifically discussed herein are preferred.

DNA segments containing a gene encoding the fusion protein are preferably obtained from recombinant DNA molecules (plasmid vectors) containing that gene. A vector that directs the expression of a fusion protein gene in a host cell is referred to herein as an "expression vector".

An expression vector contains expression control elements including the promoter. The fusion protein-coding gene is operatively linked to the expression vector to permit the promoter sequence to direct RNA polymerase binding and expression of the fusion protein-encoding gene. Useful in expressing the polypeptide coding gene are promoters that are inducible, viral, synthetic, constitutive as described by Poszkowski et al. (1989) *EMBO J.*, 3:2719 and Odell et al. (1985) *Nature*, 313:810, as well as temporally regulated, spatially regulated, and spatiotemporally regulated as given in Chua et al. (1989) *Science*, 244:174-181.

Expression vectors compatible with eukaryotic cells, such as those compatible with yeast cells or those compatible with cells of mammals, algae or insects and the like, are contemplated herein. Such expression vectors can also be used to form the recombinant DNA molecules of the present invention. Vectors for use in yeasts such as *S. cerivisiae* or *Pichia pastoris* can be episomal or integrating, as is well known. Eukaryotic cell expression vectors are well known in the art and are available from several commercial sources. Normally, such vectors contain one or more convenient restriction sites for insertion of the desired DNA segment and promoter sequences. Optionally, such vectors contain a selectable marker specific for use in eukaryotic cells. Exemplary promoters for use in *S. cerevisiae* include the *S. cerevisiae* phosphoglyceric acid kinase (PGK) promoter and the divergent promoters GAL 10 and GAL 1, whereas the alcohol oxidase gene (AOX1) is a useful promoter for *Pichia pastoris*. Illustrative expression of a fusion protein in *S. cerivisiae* and *Pichia pastoris* are shown hereinafter.

Production of a fusion protein by recombinant DNA expression in mammalian cells is illustrated hereinafter using a recombinant DNA vector that expresses the fusion protein gene in Chinese hamster ovary (CHO) host cells, Cos1 monkey host and human 293T host cells and. This is accomplished using procedures that are well known in the art and are described in more detail in Sambrook et al., *Molecular Cloning: A Laboratory Manual*, $2^{nd}$ ed., Cold Spring Harbor Laboratories (1989).

An insect cell system can also be used to express a contemplated fusion protein. For example, in one such system *Autographa californica* nuclear polyhedrosis virus (AcNPV) or baculovirus is used as a vector to express foreign genes in *Spodoptera frugiperda* cells or in *Trichoplusia larvae*. The sequences encoding a fusion protein can be cloned into a non-essential region of the virus, such as the polyhedrin gene, and placed under control of the polyhedrin promoter. Successful insertion of a fusion protein sequence renders the polyhedrin gene inactive and produces recombinant virus lacking coat protein. The recombinant viruses can then be used to infect, for example, *S. Frugiperda* cells or *Trichoplusia larvae* in which the fusion protein can be expressed. E. Engelhard et al. (1994) *Proc. Natl. Acad. Sci., USA*, 91:3224-3227; and V. Luckow, Insect Cell Expression Technology, pp. 183-218, in *Protein Engineering: Principles and Practice*, J.

L. Cleland et al. eds., Wiley-Liss, Inc, 1996). Heterologous genes placed under the control of the polyhedrin promoter of the *Autographa californica* nuclear polyhedrosis virus (AcNPV) are often expressed at high levels during the late stages of infection.

Recombinant baculoviruses containing the fusion protein gene are constructed using the baculovirus shuttle vector system (Luckow et al. (1993) *J. Virol.*, 67:4566-4579], sold commercially as the Bac-To-Bac☐ baculovirus expression system (Life Technologies). Stocks of recombinant viruses are prepared and expression of the recombinant protein is monitored by standard protocols (O'Reilly et al., *Baculovirus Expression Vectors: A Laboratory Manual*, W.H. Freeman and Company, New York, 1992; and King et al., *The Baculovirus Expression System: A Laboratory Guide*, Chapman & Hall, London, 1992).

The choice of which expression vector and ultimately to which promoter a fusion protein-encoding gene is operatively linked depends directly on the functional properties desired, e.g. the location and timing of protein expression, and the host cell to be transformed. These are well known limitations inherent in the art of constructing recombinant DNA molecules. However, a vector useful in practicing the present invention can direct the replication, and preferably also the expression (for an expression vector) of the fusion protein gene included in the DNA segment to which it is operatively linked.

The expressed RPBLAs and their fusion proteins can be obtained from the expressing host cells by usual means utilized in biochemical or biological recovery. Because the RPBLAs are dense relative to the other proteins present in the host cells, the RPBLAs are particularly amenable to being collected by centrifugation of a cellular homogenate. The fusion proteins can be obtained from the collected RPBLAs by dissolution of the surrounding membrane in a buffer containing a reducing agent such as 2-mercaptoethanol.

Without further elaboration, it is believed that one skilled in the art can, using the preceding description and the detailed examples below, utilize the present invention to its fullest extent. The following preferred specific embodiments are, therefore, to be construed as merely illustrative, and not limiting of the remainder of the disclosure in any way whatsoever.

EXAMPLE 1

Accumulation of Fusion Proteins in Transfected Mammal Cells

The synthetic genes corresponding to the mature calcitonin (Ct) and EGF sequences as well the cDNA encoding the hGH sequence, were fused to the N-terminal gamma-zein coding sequence RX3 (WO2004003207) and were introduced into the vector pcDNA3.1 (Invitrogen) to obtain the constructs p3.1RX3Ct, p3.1RX3EGF and p3.1RX3hGH. These constructs that code for the fusion proteins RX3-Ct, RX3-EGF and RX3-hGH, were introduced in 293T, Cos1 and CHO mammal cultured cells by the lipofectamine based transfection method (Invitrogen). 293T and Cos1 cells transfected with plasmid pECFP-N1 (Clontech) containing the gene sequence of an enhanced cyan fluorescent modified GFP, were used as controls.

The accumulation of fusion proteins in the transiently transfected cells was analyzed by Western blot, using antibodies raised against gamma-zein. After 44 hours of transfection, total soluble proteins were extracted with buffer A (100 mM Tris-HCl pH 8.0, 150 mM NaCl, 5 mM EDTA, 0.5% SDS, 0.5% Triton X-100, 2% 2-mercaptoethanol and protease inhibitors). Aliquots of the cell incubation media were precipitated and stored at −20° C. Proteins extracted from equivalent amounts of transfected cells were separated by SDS polyacrylamide gel electrophoresis and transferred to nitrocellulose sheets.

As can be seen from the results depicted in FIG. 1, the three fusion proteins analyzed RX3-Ct, RX3-EGF and RX3-hGH, accumulated very efficiently irrespective to the cultured cell type selected for expression: compare the pattern of RX3-hGH accumulated in both, 293T and CHO cultured cells, and the pattern of RX3-EGF in CHO and Cos1 cells. The fusion proteins were observed in the protein extracts corresponding to transfected cells (lanes c), and no immunoreactive band was detected in cell culture media (lanes m). This observation suggests that the RX3 domain is able to assemble and to retain the fusion proteins in the endomembrane compartment.

These results illustrate how the RX3-derived fusion proteins assemble and accumulate in the endomembrane system in the three types of mammalian cells analyzed (human 293T cells, monkey Cos1 cells and hamster CHO cells), suggesting that an efficient accumulation of a desired protein can be achieved in whatever mammalian cell or organism chosen via the fusion with RX3 domain.

EXAMPLE 2

Subcellular Localization of Fusion Proteins in Transfected Mammal Cells

In determine if the N-terminal gamma-zein sequence RX3 was able to induce recombinant protein body-like assemblies in mammal cells, the localization of RX3-Ct and RX3-EGF fusion proteins was analyzed by immunocytochemistry using confocal microscopy. Transfected cells were fixed for 10 minutes in 3.7% paraformaldehyde and after washing with saline phosphate buffer, were incubated with gamma-zein antiserum (dilution 1/700) for 1 hour. Non-immune serum was used as control. The primary antibodies were detected with anti-rabbit antibodies conjugated to Alexa Fluor 488 or Alexa Fluor 555 dyes (Molecular probes).

Micrographs from the transfected cells were obtained by using a confocal laser scanning microscope (Leica TCS SP, Heidelberg, Germany) fitted with spectrophotometers for emission band wavelength selection. Green fluorescent images were collected at 488 nm excitation with the Argon ion laser by using an emission window set at 495-535 nm. Red fluorescent images were collected after 543 nm excitation with a HeNe laser and emission window 550-600. Optical sections were 0.5 µm thick. Digital images and projections were recorded by using the confocal microscope software.

Figure 2:
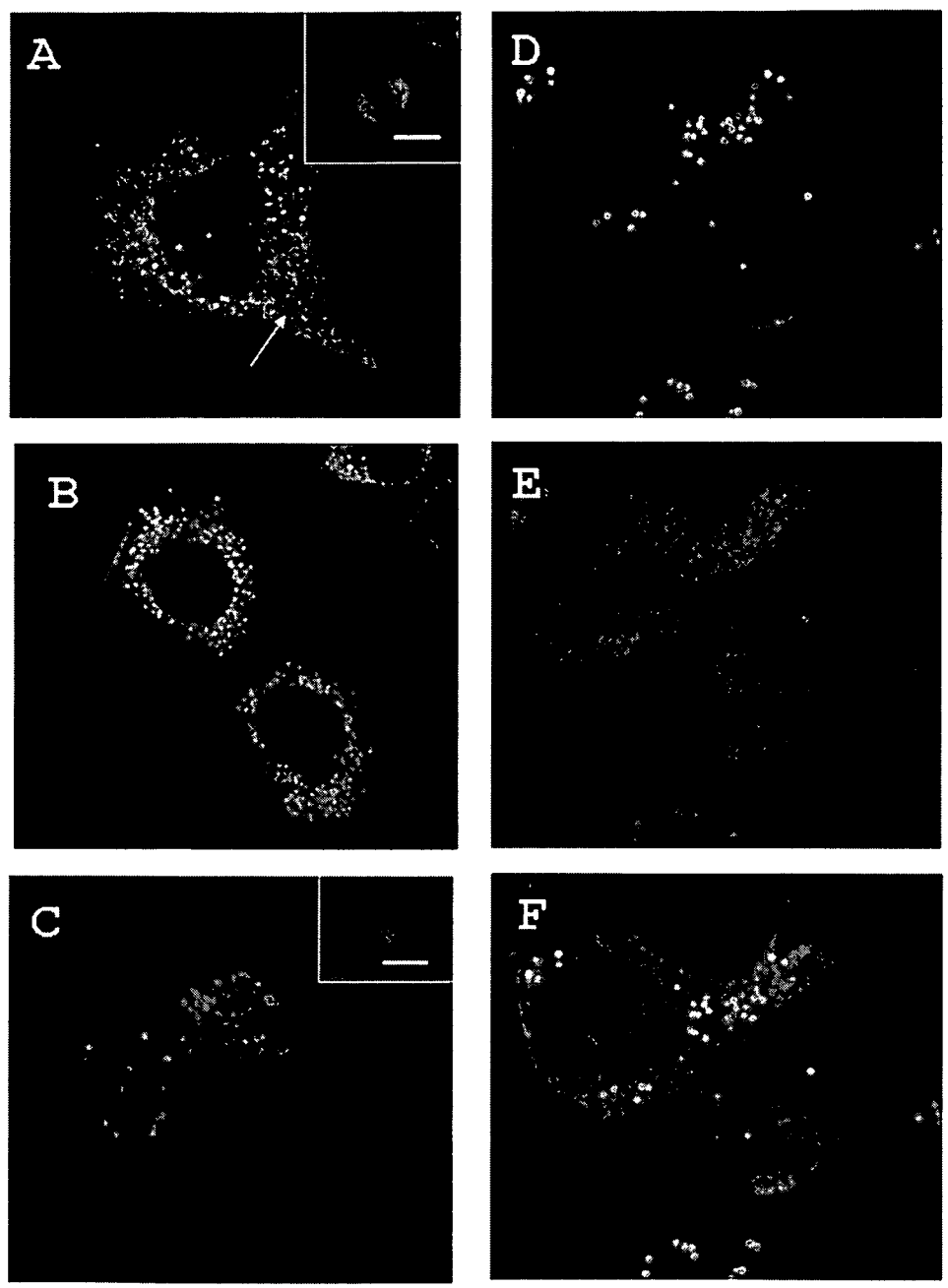
FIG. 2 is a photograph in six panels (A-F) showing the localization of fusion proteins in RPBLAs within transfected cells. Confocal microscopy was used to show Cos1 cells expressing RX3—CT (FIG. 2A), CHO cells expressing RX3-Ct (FIG. 2B) and RX3-EGF (FIG. 2C), and 293T cells coexpressing RX3-Ct and DsRed2-ER marker protein (FIG. 2D, FIG. 2E and FIG. 2F). RX3-derived fusion proteins were immunolocalized, using anti-gamma-zein serum in protein body-like structures (FIGS. 2A-2D) and in endoplasmic reticulum (see arrow in FIG. 2A).

FIG. 2 shows confocal projections of p3.1Ct- and p3.1RX3EGF-transfected cells. As shown in the figure, the corresponding fusion proteins, RX3-Ct and RX3EGF, were detected in the endoplasmic reticulum (ER, arrow in FIG. 2A)) indicating that the gamma-zein signal peptide is functional in mammal cells where it mediates the translocation of the fusion protein into the ER. The samples incubated with the non-immune serum used as control did not show any significant fluorescence (not shown).

It is important to note that surprisingly the fusion proteins appear preferentially accumulated in big spots apparently surrounded by a membrane (see inset in FIG. 2A). These structures, that are absent in non-transfected cells, are comparable in size to plant protein bodies, having diameters around 1 micron (insets in A and C). This result is not only surprising by the fact that animal cells can reproduce the PB storage organelle described in plants, but by the high number of RPBLAs observed in all transfected cells, indicating the efficient accumulation capacity of these cells. Moreover, different transfected cell types exhibited comparable localization and accumulation patterns of fusion proteins (see FIGS. 2A, 2B and 2D), and this pattern appears independent of the target fused to the PBIS (FIGS. 2B and 2C).

The cells were cotransfected with plasmid pDsRed2-ER (Clontech) containing the sequence for a fluorescent protein used as an ER marker to analyze the subcellular origin of the induced PBLS. Interestingly, as can be seen in the FIGS. 2D, 2E and 2F both, RX3-Ct and the ER marker, colocalize in the ER and in the PB-like assemblies, indicating the ER origin of the induced RPBLAs in mammal cells as occurs in plant cells.

EXAMPLE 3

Accumulation of Fusion Proteins in Transformed Yeast Cells

The sequences encoding EGF and hGH, were fused to the N-terminal gamma-zein coding sequence RX3 (WO2004003207) and were introduced into the vector pYX243 (R&D systems) to obtain the constructs c117 and c118. These constructs that code for the fusion proteins RX3-EGF and RX-hGH were introduced in *Saccharomyces cerevisiae*.

Figure 3:
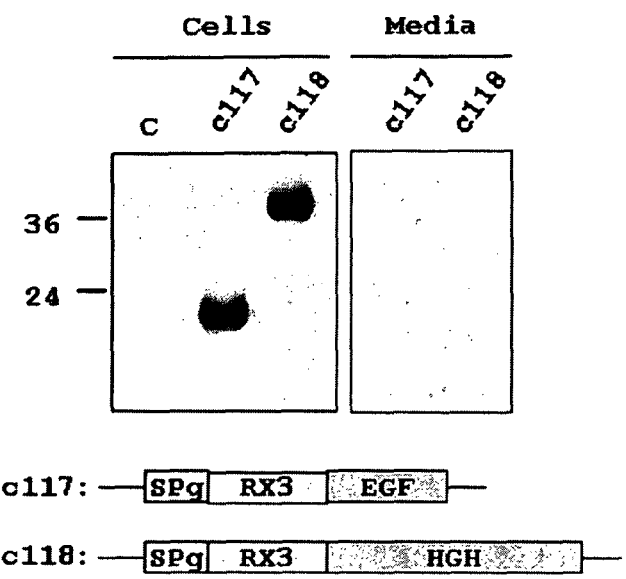
FIG. 3 in two panels (A and B) illustrates the accumulation of fusion proteins in transformed yeast cells.
Figure 3:
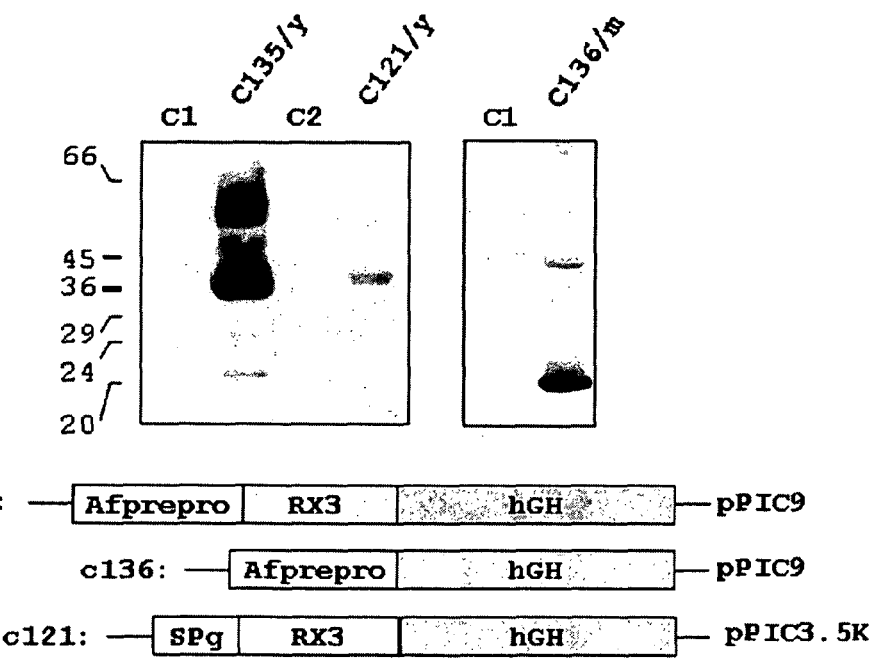

Expression analyses were made by growing the transformants in galactose-containing medium and equivalent amounts of both, cells and media, were analyzed by SDS-PAGE and immunoblot by using specific antibodies against the recombinant expressed proteins. As can be seen in FIG. 3A both RX3-EGF (lanes c117) and RX3-hGH (lanes c118) fusion proteins accumulated in the yeast cells, no traces of protein being detected in the media.

Accumulation of hGH and hGH-derived fusions was also studied in the yeast *Pichia pastoris* that was transformed with constructs c135 and c121 (coding for the fusion RX3-hGH protein) and c136 (coding for hGH protein, see schematic representation in FIG. 3B). Transformants accumulating the highest levels of recombinant proteins were selected.

Two different signal peptides were used to express the fusion protein, the gamma-zein signal peptide (FIG. 3B, SPg) and the yeast alfa factor prepro peptide (FIG. 3B, Afprepro). In addition, a control of secretion by using the yeast alfa factor prepro peptide fused directly to the hGH was also analyzed (FIG. 3B, c136). Total proteins from cells and media were analyzed by Western blot by using specific antibodies against hGH raised in rabbit.

As expected, hGH was secreted into the medium (FIG. 3B, lane c136/m) when the Afprepro peptide was used. In contrast, the fusion protein RX3-hGH accumulated inside yeast cells irrespective of the signal peptide used. As can be seen in FIG. 3B, the fusion protein was inside cells in both cases, when using the yeast Afprepro peptide (lane c135/y) and when using the gamma-zein signal peptide (lane c121/y), no traces of the protein being detected in the media (not shown). Thus, the N-terminal proline rich domain of gamma-zein was sufficient to mediate protein retention in the endomembrane compartment of yeast cells, and more particularly in a dense fraction corresponding to PB like structures that could be separated by centrifugation.

The results obtained in *Saccharomyces cerevisiae* and *Pichia pastoris* are examples of other eukaryotic organism different from plants and animals kingdoms where a fusion proteins containing a seed storage protein assemble and accumulate efficiently in PB like structures.

Experimental Procedures

Plasmid Constructs for Mammal Transfection

The synthetic gene corresponding to the mature calcitonin sequence (Ct) was obtained as described (patent application WO2004003207).

The synthetic gene encoding the 53 amino acids of active hEGF was obtained by primer overlap extension PCR method, using 4 oligonucleotides of about 60 bases, with 20 overlapping bases. The synthetic hEGF cDNA included a 5' linker sequence corresponding to the Factor Xa specific cleavage site. The oligonucleotides were purified by polyacrilamide denaturing gel.

```
                                    SEQ ID NO: 25
EGF1:
5' CATGCCATGGGAATTGAGGGTAGGAACTCTGATTCAGAATGCCCACT
CAGTCACGACGGA TATT 3'

SEQ ID NO: 26
EGF2:
5' ACTTGTCCAAGGCCTCGATGTACATGCATACCCCATCGTGAAGACAA
TATCCGTCGTGACTGAGT 3'

SEQ ID NO: 27
EGF3:
5' CATCGAGGCCTTGGACAAGTACGCATGTAATTGTGTAGTGGGATACA
TTGGTGAACGCTGTCAGT 3'

SEQ ID NO: 28
EGF4:
5' TCAGGATCCTTATCACCTAAGCTCCCACCATTTCAAGTCTCGATACT
GACAGCGTTCACCAATGT
```

The cDNA sequence encoding the 191 amino acids of human Growth Hormone (hGH) was obtained from cDNA of human pituitary gland (Clontech, BDBiosciences) by PCR using the oligonucleotides GH5:

```
                                    SEQ ID NO: 29
5' GTCCATGGACGACGATGATAAGTTCCCAACCATTCCCTTATCCA 3'
and
                                    SEQ ID NO: 30
GH3: 5' TCAGGATCCTTATCAGAAGCCACAGCTGCCCTCCA 3'
``` that included the sequence corresponding to the enterokinase cleavage site.

The synthetic genes corresponding to the mature calcitonin (Ct, WO2004003207) and hEGF sequences as well the cDNA encoding the hGH were fused to the RX3 N-terminal gamma-zein coding sequence (patent WO2004003207) and were introduced into pUC18. SalI-BamHI restriction fragments from the pUC18 derived plasmids pUC18RX3Ct, pUC18RX3EGF and pUC18RX3gHG, containing the corresponding fusion protein RX3-Ct, RX3-EGF and RX3-hGH sequences were introduced in the vector pcDNA3.1-(Invitrogen) restricted with Xho I-Bam HI. In the resulting constructs named p3.1RX3CT, p3.1RX3EGF and p3.1RX3hGH, the fusion protein sequences were under the CMV promoter and the terminator pA BGH.

Plasmid Constructs for Yeast Transformation

Host Strains and Vectors:

The *Saccharomyces cerevisiae* strain (genotype Mata his3 leu2 met15 ura3 bar1::URA3) was transformed by using the vector pYX243 (GAL promoter, LEU2, AmpR, from R&D Systems) derived constructs. The *Pichia pastoris* strain GS115 (his4) and the vectors pPIC9 and pPIC3.5K (AOX1 promoter, HIS4, AmpR) were from Invitrogen life tech.

Plasmid Constructs:

SalI(blunt ended)-BamHI restriction fragments from the pUC18-derived plasmids pUC18RX3EGF and pUC18RX3hGH described above, containing the corresponding fusion protein RX3-EGF and RX3-hGH sequences were introduced in the vector pYX243 (R&D Systems) restricted with EcoRI (blunt ended)-Bam HI. In the resulting constructs named, respectively, c117 and c118, the fusion protein sequences were under the inducible GAL promoter.

SalI(blunt ended)-BamHI (blund ended) restriction fragments from the pUC18 derived plasmids pUC18RX3EGF and pUC18RX3hGH, were introduced in the vector pPIC3.5K (Invitrogen) restricted with NotI (blunt ended)-EcoRI (blunt ended) to obtain plasmids c120 and c121 to transform Pichia Pastoris.

Plasmid pPIC9 (Invitrogen) was used to analyze fusion protein expression using a yeast signal peptide, the alfa prepro peptide of Saccharomyces. XhoI-NotI flanked sequences coding for RX3-hGH and hGH proteins were obtained by PCR using pUC18RX3hGH as template and the following oligonucleotides:

```
                                       SEQ ID NO: 31
af06, 5' GCTCTCGAGAAAAGATTCCCAACCATTCCCTTATCC 3';

SEQ ID NO: 32
afRX, 5' GCTCTCGAGAAAAGAACGCATACAAGCGGCGGCTGC 3';

SEQ ID NO: 33
06Not, 5' CTTCGCGGCCGCTTATCAGAAGCCACAGCTGCC 3'
```

These sequences contained the sequence coding for the site KEX2 necessary for efficient cleavage of the alfa prepro peptide (Invitrogen, Pichia expression Kit). The PCR products were cloned in pPIC9 restricted with XhoI-NotI giving the plasmids c135 and c136 containing, respectively, the RX3-hGH and the hGH protein sequences fused to the alfa factor prepro peptide.

Yeast Transformation

The Saccharomyces cerevisiae strain (leu2) was transformed with the plasmid constructs c117 and c118 by the LiAc Method (Ito et al. 1983, J. Bacteriol. 153:163-168) and transformants were selected on Leu⁻ plates. Expression analyses were made by growing the transformants in a galactose containing medium (demanar composició.)

The Pichia pastoris strain GS115 (his4) was transformed by the Pichia EasyComp Kit (Invitrogen life tech.) with SacI linearized c120 and c121 plasmids and plated on RDB His⁻ medium. Mut phenotypes were determined by streaking the colonies onto MD and MM agar plates. Expression trials were performed by growing the transformants in YPD medium for two days. Thereafter, the cells were sedimented and suspended in MM medium for another 48 hours and methanol was added to a final concentration of 0.5% every 24 hours. Transformants accumulating the highest levels of recombinant protein were selected. Media recipes were as described by Invitrogen (Pichia expression Kit).

Yeast Proteins Extraction and Western Blot

S. cerevisiae and P. pastoris expressing recombinant fusion proteins were pelleted. Aliquots of the respective incubation media were precipitated and stored at −20° C. to be analyzed. The cell pellets were also frozen and after thawing, the cells were broken by standard methods using glass beads and medium H (50 mM HCl-Tris pH 8.0, 150 mM NaCl, 5 mM EDTA, 200 mM DTT and protease inhibitors). Equivalent amounts of both, cells and media, were analyzed by SDS-PAGE and immunoblot by using specific antibodies against the recombinant expressed proteins.

Each of the patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. An isolated transformed host animal cell that contains an expressed and stably accumulated recombinant fusion protein within recombinant protein body-like assemblies (RPBLAs), said RPBLAs having a diameter of about 1 micron, said fusion protein comprising at least a protein body-inducing sequence heterologous to the host animal cell and a product of interest; wherein the protein body-inducing sequence is a prolamin or an RX3 domain.

2. The host cell according to claim 1 wherein said density of the RPBLAs is about 1.1 to about 1.35 g/ml.

3. The host cell according to claim 1 wherein said fusion protein further includes a linker sequence between the protein body-inducing sequence and the sequence of the product of interest.

4. The host cell according to claim 1 wherein the prolamin sequence is gamma-zein, alpha-zein or rice prolamin.

5. A method of producing a fusion protein comprising:
   (a) transforming an isolated animal cell with a nucleic acid sequence that encodes said fusion protein comprising (i) a first nucleic acid coding for a protein body-inducing sequence (PBIS) that is operatively linked in frame to (ii) a second nucleic acid comprising a nucleotide sequence coding for a polypeptide product of interest; wherein the protein body-inducing sequence is a prolamin or an RX3 domain; and
   (b) maintaining the transformed animal cell for a time period and under culture conditions suitable for expression of the fusion protein, stable accumulation of said expressed fusion protein and assembly of the expressed fusion protein into recombinant protein body-like assemblies (RPBLAs) having a diameter of about 1 micron.

6. The method according to claim 5 wherein the 3' end of the first nucleic acid sequence (i) is linked to the 5' end of the second nucleic acid sequence (ii).

7. The method according to claim 5 wherein said nucleic acid encoding said fusion protein further encodes a linker sequence between the PBIS and polypeptide product of interest.

8. The method according to claim 5 including the further step of recovering the expressed fusion protein.

9. The method according to claim 5 wherein the prolamin sequence is gamma-zein, alpha-zein or rice prolamin.

10. The method according to claim 5 wherein the nucleic acid sequence used for transforming the host cells is present in an expression vector that includes one or more regulatory sequences.

11. The method according to claim 10 wherein said one or more regulatory sequences includes a promoter.

12. A transformed host algal cell that contains an expressed and stably accumulated recombinant fusion protein within recombinant protein body-like assemblies (RPBLAs), said RPBLAs having a diameter of about 1 micron, said fusion protein comprising at least a protein body-inducing sequence heterologous to the host algal cell and a product of interest; wherein the protein body-inducing sequence is a prolamin or an RX3 domain.

13. The host cell according to claim 12 wherein said density of the RPBLAs is about 1.1 to about 1.35 g/ml.

14. The host cell according to claim 12 wherein said fusion protein further includes a linker sequence between the protein body-inducing sequence and the sequence of the product of interest.

15. The host cell according to claim 12 wherein the prolamin sequence is gamma-zein, alpha-zein or rice prolamin.

16. A method of producing a fusion protein comprising:
   (a) transforming an algal cell with a nucleic acid sequence that encodes said fusion protein comprising (i) a first nucleic acid coding for a protein body-inducing sequence (PBIS) that is operatively linked in frame to (ii) a second nucleic acid comprising the nucleotide sequence coding for a polypeptide product of interest; wherein the protein body-inducing sequence is a prolamin or an RX3 domain; and
   (b) maintaining the transformed algal cell for a time period and under culture conditions suitable for expression of the fusion protein, stable accumulation of said expressed fusion protein and assembly of the expressed fusion protein into recombinant protein body-like assemblies (RPBLAs) having a diameter of about 1 micron.

17. The method according to claim 16 wherein the 3' end of the first nucleic acid sequence (i) is linked to the 5' end of the second nucleic acid sequence (ii).

18. The method according to claim 16 wherein said nucleic acid encoding said fusion protein further encodes a linker sequence between the PBIS and polypeptide product of interest.

19. The method according to claim 16 including the further step of recovering the expressed fusion protein.

20. The method according to claim 16 wherein the prolamin sequence is gamma-zein, alpha-zein or rice prolamin.

21. The method according to claim 16 wherein the nucleic acid sequence used for transforming the host cells is present in an expression vector that includes one or snore regulatory sequences.

22. The method according to claim 21 wherein said one or more regulatory sequences includes a promoter.

23. The host cell of claim 1, wherein the host cell is a mammalian cell.

24. The host cell of claim 23, wherein the mammalian cell is a CHO cell.

25. The host cell of claim 23, wherein the mammalian cell is a COS1 cell.

26. The host cell of claim 23, wherein the mammalian cell is a 293 cell.

27. The method of claim 5, wherein the animal cell is a mammalian cell.

28. The method of claim 27, wherein the mammalian cell is a CHO cell.

29. The method of claim 27, wherein the mammalian cell is a COS1 cell.

30. The method cell of claim 27, wherein the mammalian cell is a 293 cell.

31. The host cell of claim 1, wherein the host cell in an insect cell.

32. Tne host cell of claim 31, wherein the insect cell is a Spodoptera frugiperda cell.

33. The host cell of claim 31, wherein the insect cell is a Trichoplusia cell.

34. The method of claim 5, wherein the animal cell is an insect cell.

35. The method of claim 34, wherein the insect cell is a Spodoptera frugiperda cell.

36. The method of claim 34, wherein the insect cell is a Trichoplusia cell.

37. The host cell of claim 1, wherein the protein body-inducing sequence is an RX3 domain.

38. The method of claim 5, wherein the protein body-inducing sequence is an RX3 domain.

39. The host cell of claim 12, wherein the protein body-inducing sequence is an RX3 domain.

40. The method of claim 16, wherein the protein body-inducing sequence is an RX3 domain.

41. The host cell of claim 1, wherein the protein body-inducing sequence is a prolamin.

42. The method of claim 5, wherein the protein body-inducing sequence is a prolamin.

43. The host cell of claim 12, wherein the protein body-inducing sequence is a prolamin.

44. The method of claim 16, wherein the protein body-inducing sequence is a prolamin.

* * * * *

SEQUENCE LISTING

```
<160> NUMBER OF SEQ ID NOS: 33

<210> SEQ ID NO 1
<211> LENGTH: 6
<212> TYPE: PRT
<213> ORGANISM: Artificial sequence
<220> FEATURE:
<223> OTHER INFORMATION: part of Promoter 2xCaMV

<400> SEQUENCE: 1

Pro Pro Pro Val His Leu
1               5

<210> SEQ ID NO 2
<211> LENGTH: 52
<212> TYPE: PRT
<213> ORGANISM: Artificial sequence
<220> FEATURE:
<223> OTHER INFORMATION: RX3 query aa sequence

<400> SEQUENCE: 2

Pro Pro Pro Pro Val His Leu Pro Pro Pro Val His Leu Pro Pro Pro
1               5                   10                  15

Val His Leu Pro Pro Pro Val His Leu Pro Pro Pro Val His Leu Pro
            20                  25                  30
```

```
Pro Pro Val His Leu Pro Pro Val His Val Pro Pro Val His
            35                  40                  45

Leu Pro Pro Pro
    50

<210> SEQ ID NO 3
<211> LENGTH: 65
<212> TYPE: PRT
<213> ORGANISM: Artificial sequence
<220> FEATURE:
<223> OTHER INFORMATION: Alpha zein aa sequence

<400> SEQUENCE: 3

Gln Gln Gln Gln Gln Phe Leu Pro Ala Leu Ser Gln Leu Asp Val Val
1               5                   10                  15

Asn Pro Val Ala Tyr Leu Gln Gln Gln Leu Leu Ala Ser Asn Pro Leu
            20                  25                  30

Ala Leu Ala Asn Val Ala Ala Tyr Gln Gln Gln Gln Leu Gln Gln
        35                  40                  45

Phe Leu Pro Ala Leu Ser Gln Leu Ala Met Val Asn Pro Ala Ala Tyr
    50                  55                  60

Leu
65

<210> SEQ ID NO 4
<211> LENGTH: 70
<212> TYPE: PRT
<213> ORGANISM: Artificial sequence
<220> FEATURE:
<223> OTHER INFORMATION: rice prolamin query aa sequence

<400> SEQUENCE: 4

Gln Gln Val Leu Ser Pro Tyr Asn Glu Phe Val Arg Gln Gln Tyr Gly
1               5                   10                  15

Ile Ala Ala Ser Pro Phe Leu Gln Ser Ala Thr Phe Gln Leu Arg Asn
            20                  25                  30

Asn Gln Val Trp Gln Gln Leu Ala Leu Val Ala Gln Gln Ser His Cys
        35                  40                  45

Gln Asp Ile Asn Ile Val Gln Ala Ile Ala Gln Gln Leu Gln Leu Gln
    50                  55                  60

Gln Phe Gly Asp Leu Tyr
65                  70

<210> SEQ ID NO 5
<211> LENGTH: 672
<212> TYPE: DNA
<213> ORGANISM: Maize

<400> SEQUENCE: 5
atgagggtgt tgctcgttgc cctcgctctc ctggctctcg ctgcgagcgc cacctccacg      60
catacaagcg gcggctgcgg ctgccagcca ccgccgccgg ttcatctacc gccgccggtg     120
catctgccac ctccggttca cctgccacct ccggtgcatc tcccaccgcc ggtccacctg     180
ccgccgccgg tccacctgcc accgccggtc catgtgccgc cgccggttca tctgccgccg     240
ccaccatgcc actaccctac tcaaccgccc cggcctcagc ctcatcccca gccacaccca     300
tgcccgtgcc aacagccgca tccaagcccg tgccagctgc agggaacctg cggcgttggc     360 agcacccga tcctgggcca gtgcgtcgag tttctgaggc atcagtgcag cccgacggcg     420 acgcctact gctcgcctca gtgccagtcg ttgcggcagc agtgttgcca gcagctcagg     480
```

```
caggtggagc cgcagcaccg gtaccaggcg atcttcggct tggtcctcca gtccatcctg      540
cagcagcagc cgcaaagcgg ccaggtcgcg gggctgttgg cggcgcagat agcgcagcaa      600
ctgacggcga tgtgcggcct gcagcagccg actccatgcc cctacgctgc tgccggcggt      660
gtcccccacg cc                                                          672
```

<210> SEQ ID NO 6
<211> LENGTH: 224
<212> TYPE: PRT
<213> ORGANISM: Maize

<400> SEQUENCE: 6

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Val His Leu Pro Pro Val His Leu Pro Pro Val His Leu
            35                  40                  45

Pro Pro Pro Val His Leu Pro Pro Val His Leu Pro Pro Val
50                  55                  60

His Leu Pro Pro Pro Val His Val Pro Pro Val His Leu Pro Pro
65                  70                  75                  80

Pro Pro Cys His Tyr Pro Thr Gln Pro Arg Pro Gln Pro His Pro
                85                  90                  95

Gln Pro His Pro Cys Pro Cys Gln Gln Pro His Pro Ser Pro Cys Gln
            100                 105                 110

Leu Gln Gly Thr Cys Gly Val Gly Ser Thr Pro Ile Leu Gly Gln Cys
        115                 120                 125

Val Glu Phe Leu Arg His Gln Cys Ser Pro Thr Ala Thr Pro Tyr Cys
    130                 135                 140

Ser Pro Gln Cys Gln Ser Leu Arg Gln Cys Cys Gln Gln Leu Arg
145                 150                 155                 160

Gln Val Glu Pro Gln His Arg Tyr Gln Ala Ile Phe Gly Leu Val Leu
                165                 170                 175

Gln Ser Ile Leu Gln Gln Pro Gln Ser Gly Gln Val Ala Gly Leu
            180                 185                 190

Leu Ala Ala Gln Ile Ala Gln Gln Leu Thr Ala Met Cys Gly Leu Gln
        195                 200                 205

Gln Pro Thr Pro Cys Pro Tyr Ala Ala Ala Gly Gly Val Pro His Ala
    210                 215                 220
```

<210> SEQ ID NO 7
<211> LENGTH: 339
<212> TYPE: DNA
<213> ORGANISM: Artificial sequence
<220> FEATURE:
<223> OTHER INFORMATION: RX3 DNA sequence

<400> SEQUENCE: 7

```
atgagggtgt tgctcgttgc cctcgctctc ctggctctcg ctgcgagcgc cacctccacg       60
catacaagcg gcggctgcgg ctgccagcca ccgccgccgg ttcatctacc gccgccgtg      120 catctgccac ctccggttca cctgccacct ccggtgcatc tcccaccgcc ggtccacctg      180
ccgccgccgg tccacctgcc accgccggtc catgtgccgc cgccggttca tctgccgccg      240
ccaccatgcc actaccctac tcaaccgccc ggcctcagc ctcatcccca gccacaccca      300
```
tgcccgtgcc aacagccgca tccaagcccg tgccagacc 339

<210> SEQ ID NO 8
<211> LENGTH: 113
<212> TYPE: PRT
<213> ORGANISM: Artificial sequence
<220> FEATURE:
<223> OTHER INFORMATION: RX3 aa

<400> SEQUENCE: 8

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Pro Val His Leu
        35                  40                  45

Pro Pro Pro Val His Leu Pro Pro Pro Val His Leu Pro Pro Pro Val
    50                  55                  60

His Leu Pro Pro Pro Val His Val Pro Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110

Tyr

<210> SEQ ID NO 9
<211> LENGTH: 240
<212> TYPE: DNA
<213> ORGANISM: Artificial sequence
<220> FEATURE:
<223> OTHER INFORMATION: R3 DNA

<400> SEQUENCE: 9
atgagggtgt tgctcgttgc cctcgctctc ctggctctcg ctgcgagcgc cacctccacg      60
catacaagcg gcggctgcgg ctgccagcca ccgccgccgg ttcatctacc gccgccggtg     120
catctgccac ctccggttca cctgccacct ccggtgcatc tcccaccgcc ggtccacctg     180
ccgccgccgg tccacctgcc accgccggtc catgtgccgc cgccggttca tctgccgccg     240

<210> SEQ ID NO 10
<211> LENGTH: 92
<212> TYPE: PRT
<213> ORGANISM: Artificial sequence
<220> FEATURE:
<223> OTHER INFORMATION: Artificial sequence

<400> SEQUENCE: 10

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Pro Val His Leu
        35                  40                  45

Pro Pro Pro Val His Leu Pro Pro Pro Val His Leu Pro Pro Pro Val
    50                  55                  60

His Leu Pro Pro Pro Val His Val Pro Pro Pro Val His Leu Pro Pro
65                  70                  75                  80

Pro Pro Cys His Tyr Pro Thr Gln Pro Pro Arg Tyr

-continued

<210> SEQ ID NO 11
<211> LENGTH: 213
<212> TYPE: DNA
<213> ORGANISM: Artificial sequence
<220> FEATURE:
<223> OTHER INFORMATION: Artificial sequence

<400> SEQUENCE: 11

```
atgagggtgt tgctcgttgc cctcgctctc ctggctctcg ctgcgagcgc cacctccacg    60
catacaagcg gcggctgcgg ctgccagcca ccgccgccgg ttcatctgcc gccgccacca   120
tgccactacc ctacacaacc gccccggcct cagcctcatc cccagccaca cccatgcccg   180
tgccaacagc cgcatccaag cccgtgccag acc                                 213
```

<210> SEQ ID NO 12
<211> LENGTH: 71
<212> TYPE: PRT
<213> ORGANISM: Artificial sequence
<220> FEATURE:
<223> OTHER INFORMATION: Artificial sequence

<400> SEQUENCE: 12

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Val His Leu Pro Pro Pro Cys His Tyr Pro Thr Gln Pro
        35                  40                  45

Arg Pro Gln Pro His Pro Gln Pro His Pro Cys Pro Cys Gln Pro
    50                  55                  60

His Pro Ser Pro Cys Gln Tyr
65                  70

<210> SEQ ID NO 13
<211> LENGTH: 180
<212> TYPE: DNA
<213> ORGANISM: Artificial sequence
<220> FEATURE:
<223> OTHER INFORMATION: Artficial sequence

<400> SEQUENCE: 13

```
atgagggtgt tgctcgttgc cctcgctctc ctggctctcg ctgcgagcgc cacctccacg    60
catacaagcg gcggctgcgg ctgccaatgc cactaccta ctcaaccgcc ccggcctcag   120
cctcatcccc agccacaccc atgcccgtgc caacagccgc atccaagccc gtgccagacc   180
```

<210> SEQ ID NO 14
<211> LENGTH: 60
<212> TYPE: PRT
<213> ORGANISM: Artificial sequence
<220> FEATURE:
<223> OTHER INFORMATION: Artificial sequence

<400> SEQUENCE: 14

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Cys His Tyr
            20                  25                  30

Pro Thr Gln Pro Pro Arg Pro Gln Pro His Pro Gln Pro His Pro Cys
        35                  40                  45

```
Pro Cys Gln Gln Pro His Pro Ser Pro Cys Gln Tyr
    50                  55                  60

<210> SEQ ID NO 15
<211> LENGTH: 150
<212> TYPE: PRT
<213> ORGANISM: Artificial sequence
<220> FEATURE:
<223> OTHER INFORMATION: Artificial sequence

<400> SEQUENCE: 15

Met Lys Ile Ile Phe Val Phe Ala Leu Leu Ala Ile Ala Ala Cys Ser
1               5                   10                  15

Ala Ser Ala Gln Phe Asp Val Leu Gly Gln Ser Tyr Arg Gln Tyr Gln
            20                  25                  30

Leu Gln Ser Pro Val Leu Leu Gln Gln Gln Val Leu Ser Pro Tyr Asn
        35                  40                  45

Glu Phe Val Arg Gln Gln Tyr Gly Ile Ala Ala Ser Pro Phe Leu Gln
50                  55                  60

Ser Ala Thr Phe Gln Leu Arg Asn Asn Gln Val Trp Gln Gln Leu Ala
65                  70                  75                  80

Leu Val Ala Gln Gln Ser His Cys Gln Asp Ile Asn Ile Val Gln Ala
                85                  90                  95

Ile Ala Gln Gln Leu Gln Leu Gln Gln Phe Gly Asp Leu Tyr Phe Asp
            100                 105                 110

Arg Asn Leu Ala Gln Ala Gln Ala Leu Leu Ala Phe Asn Val Pro Ser
        115                 120                 125

Arg Tyr Gly Ile Tyr Pro Arg Tyr Tyr Gly Ala Pro Ser Thr Ile Thr
130                 135                 140

Thr Leu Gly Gly Val Leu
145                 150

<210> SEQ ID NO 16
<211> LENGTH: 450
<212> TYPE: DNA
<213> ORGANISM: Artificial sequence
<220> FEATURE:
<223> OTHER INFORMATION: Artificial sequence

<400> SEQUENCE: 16
atgaagatca ttttcgtctt tgctctcctt gctattgctg catgcagcgc ctctgcgcag     60
tttgatgttt taggtcaaag ttataggcaa tatcagctgc agtcgcctgt cctgctacag    120
caacaggtgc ttagcccata taatgagttc gtaaggcagc agtatggcat agcggcaagc    180
cccttcttgc aatcagctac gtttcaactg agaaacaacc aagtctggca acagctcgcg    240
ctggtggcgc aacaatctca ctgtcaggac attaacattg ttcaggccat agcgcagcag    300
ctacaactcc agcagtttgg tgatctctac tttgatcgga atctggctca agctcaagct    360
ctgttggctt taacgtgcc atctagatat ggtatctacc ctaggtacta tggtgcaccc    420
agtaccatta ccacccttgg cggtgtcttg                                     450

<210> SEQ ID NO 17
<211> LENGTH: 144
<212> TYPE: PRT
<213> ORGANISM: Artificial sequence
<220> FEATURE:
<223> OTHER INFORMATION: Artificial sequence

<400> SEQUENCE: 17
```

```
Met Ala Thr Lys Ile Leu Ala Leu Leu Ala Leu Leu Ala Leu Phe Val
1               5                   10                  15

Ser Ala Thr Asn Ala Phe Ile Ile Pro Gln Cys Ser Leu Ala Pro Ser
                20                  25                  30

Ala Ile Ile Pro Gln Phe Leu Pro Pro Val Thr Ser Met Gly Phe Glu
            35                  40                  45

His Leu Ala Val Gln Ala Tyr Arg Leu Gln Gln Ala Leu Ala Ala Ser
        50                  55                  60

Val Leu Gln Gln Pro Ile Asn Gln Leu Gln Gln Gln Ser Leu Ala His
65                  70                  75                  80

Leu Thr Ile Gln Thr Ile Ala Thr Gln Gln Gln Gln Gln Phe Leu Pro
                85                  90                  95

Ala Leu Ser Gln Leu Asp Val Val Asn Pro Val Ala Tyr Leu Gln Gln
            100                 105                 110

Gln Leu Leu Ala Ser Asn Pro Leu Ala Leu Ala Asn Val Ala Ala Tyr
        115                 120                 125

Gln Gln Gln Gln Gln Leu Gln Gln Phe Leu Pro Ala Leu Ser Gln Leu
    130                 135                 140
```

<210> SEQ ID NO 18
<211> LENGTH: 432
<212> TYPE: DNA
<213> ORGANISM: Artificial sequence
<220> FEATURE:
<223> OTHER INFORMATION: Artificial sequence

<400> SEQUENCE: 18

```
atggctacca agatattagc cctccttgcg cttcttgccc ttttttgtgag cgcaacaaat      60
gcgttcatta ttccacaatg ctcacttgct cctagtgcca ttataccaca gttcctccca     120
ccagttactt caatgggctt cgaacaccta gctgtgcaag cctacaggct acaacaagcg     180
cttgcggcaa gcgtcttaca acaaccaatt aaccaattgc aacaacaatc cttggcacat     240
ctaaccatac aaaccatcgc aacgcaacag caacaacagt cctaccagc actgagccaa      300
ctagatgtgg tgaaccctgt cgcctacttg caacagcagc tgcttgcatc caacccactt     360
gctctggcaa acgtagctgc ataccaacaa caacaacaat gcagcagtt tctgccagcg      420
ctcagtcaac ta                                                         432
```

<210> SEQ ID NO 19
<211> LENGTH: 34
<212> TYPE: PRT
<213> ORGANISM: Salmon

<400> SEQUENCE: 19

```
Lys Cys Ser Asn Leu Ser Thr Cys Val Leu Gly Lys Leu Ser Gln Glu
1               5                   10                  15

Leu His Lys Leu Gln Thr Tyr Pro Arg Thr Asn Thr Gly Ser Gly Thr
                20                  25                  30

Pro Gly
```

<210> SEQ ID NO 20
<211> LENGTH: 102
<212> TYPE: DNA
<213> ORGANISM: Salmon

<400> SEQUENCE: 20

```
aagtgctcca acctctctac ctgcgttctt ggtaagctct ctcaggagct tcacaagctc      60
```

```
cagacttacc ctagaaccaa cactggttcc ggtacccctg gt                              102
```

<210> SEQ ID NO 21
<211> LENGTH: 53
<212> TYPE: PRT
<213> ORGANISM: Artificial sequence
<220> FEATURE:
<223> OTHER INFORMATION: Artificial sequence

<400> SEQUENCE: 21

```
Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

<210> SEQ ID NO 22
<211> LENGTH: 162
<212> TYPE: DNA
<213> ORGANISM: Artificial sequence
<220> FEATURE:
<223> OTHER INFORMATION: Artificial sequence

<400> SEQUENCE: 22

```
aactctgatt cagaatgccc actcagtcac gacggatatt gtcttcacga tggggtatgc          60
atgtacatcg aggccttgga caagtacgca tgtaattgtg tagtgggata cattggtgaa         120
cgctgtcagt atcgagactt gaaatggtgg gagcttaggt ga                            162
```

<210> SEQ ID NO 23
<211> LENGTH: 191
<212> TYPE: PRT
<213> ORGANISM: Artificial sequence
<220> FEATURE:
<223> OTHER INFORMATION: hGH protein

<400> SEQUENCE: 23

```
Phe Pro Thr Ile Pro Leu Ser Arg Leu Phe Asp Asn Ala Met Leu Arg
1               5                   10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
```

```
                145                 150                 155                 160
            Gly Leu Leu Tyr Cys Phe Arg Lys Asp Met Asp Lys Val Glu Thr Phe
                            165                 170                 175
            Leu Arg Ile Val Gln Cys Arg Ser Val Glu Gly Ser Cys Gly Phe
                        180                 185                 190

<210> SEQ ID NO 24
<211> LENGTH: 576
<212> TYPE: DNA
<213> ORGANISM: Artificial sequence
<220> FEATURE:
<223> OTHER INFORMATION: Artificial sequence

<400> SEQUENCE: 24
ttcccaacca ttcccttatc caggcttttt gacaacgcta tgctccgcgc ccatcgtctg      60
caccagctgg cctttgacac ctaccaggag tttgaagaag cctatatccc aaaggaacag     120
aagtattcat tcctgcagaa ccccagacc tccctctgtt tctcagagtc tattccgaca     180
ccctccaaca gggaggaaac acaacagaaa tccaacctag agctgctccg catctccctg     240
ctgctcatcc agtcgtggct ggagcccgtg cagttcctca ggagtgtctt cgccaacagc     300
ctggtgtacg gcgcctctga cagcaacgtc tatgacctcc taaaggacct agaggaaggc     360
atccaaacgc tgatggggag gctggaagat ggcagccccc ggactgggca gatcttcaag     420
cagacctaca gcaagttcga cacaaactca cacaacgatg acgcactact caagaactac     480
gggctgctct actgcttcag gaaggacatg gacaaggtcg agacattcct gcgcatcgtg     540
cagtgccgct ctgtggaggg cagctgtggc ttctga                              576

<210> SEQ ID NO 25
<211> LENGTH: 64
<212> TYPE: DNA
<213> ORGANISM: Artificial sequence
<220> FEATURE:
<223> OTHER INFORMATION: EFG1 DNA sequence

<400> SEQUENCE: 25
catgccatgg gaattgaggg taggaactct gattcagaat gcccactcag tcacgacgga      60
tatt                                                                  64

<210> SEQ ID NO 26
<211> LENGTH: 65
<212> TYPE: DNA
<213> ORGANISM: Artificial sequence
<220> FEATURE:
<223> OTHER INFORMATION: artificial sequence

<400> SEQUENCE: 26
acttgtccaa ggcctcgatg tacatgcata ccccatcgtg aagacaatat ccgtcgtgac      60
tgagt                                                                 65

<210> SEQ ID NO 27
<211> LENGTH: 65
<212> TYPE: DNA
<213> ORGANISM: Artificial sequence
<220> FEATURE:
<223> OTHER INFORMATION: Artificial sequence

<400> SEQUENCE: 27
catcgaggcc ttggacaagt acgcatgtaa ttgtgtagtg ggatacattg gtgaacgctg      60
tcagt                                                                 65
```

<210> SEQ ID NO 28
<211> LENGTH: 65
<212> TYPE: DNA
<213> ORGANISM: Artificial sequence
<220> FEATURE:
<223> OTHER INFORMATION: Artificial sequence

<400> SEQUENCE: 28
tcaggatcct tatcacctaa gctcccacca tttcaagtct cgatactgac agcgttcacc    60
aatgt    65

<210> SEQ ID NO 29
<211> LENGTH: 44
<212> TYPE: DNA
<213> ORGANISM: Artificial sequence
<220> FEATURE:
<223> OTHER INFORMATION: Artificial sequence

<400> SEQUENCE: 29
gtccatggac gacgatgata agttcccaac cattcccttaa tcca    44

<210> SEQ ID NO 30
<211> LENGTH: 35
<212> TYPE: DNA
<213> ORGANISM: Artificial sequence
<220> FEATURE:
<223> OTHER INFORMATION: Artificial sequence

<400> SEQUENCE: 30
tcaggatcct tatcagaagc cacagctgcc ctcca    35

<210> SEQ ID NO 31
<211> LENGTH: 36
<212> TYPE: DNA
<213> ORGANISM: Artificial sequence
<220> FEATURE:
<223> OTHER INFORMATION: Artificial sequence

<400> SEQUENCE: 31
gctctcgaga aaagattccc aaccattccc ttatcc    36

<210> SEQ ID NO 32
<211> LENGTH: 36
<212> TYPE: DNA
<213> ORGANISM: Artificial sequence
<220> FEATURE:
<223> OTHER INFORMATION: Artificial sequence

<400> SEQUENCE: 32
gctctcgaga aaagaacgca tacaagcggc ggctgc    36

<210> SEQ ID NO 33
<211> LENGTH: 33
<212> TYPE: DNA
<213> ORGANISM: Artificial sequence
<220> FEATURE:
<223> OTHER INFORMATION: Artificial sequence

<400> SEQUENCE: 33
cttcgcggcc gcttatcaga agccacagct gcc    33